USO10287594B2

United States Patent
Beetham et al.

(10) Patent No.: US 10,287,594 B2
(45) Date of Patent: *May 14, 2019

(54) METHODS AND COMPOSITIONS FOR INCREASING EFFICIENCY OF TARGETED GENE MODIFICATION USING OLIGONUCLEOTIDE-MEDIATED GENE REPAIR

(71) Applicants: CIBUS US LLC, San Diego, CA (US); CIBUS EUROPE B.V., AD Kapelle (NL)

(72) Inventors: Peter R. Beetham, Carlsbad, CA (US); Gregory F. W. Gocal, San Diego, CA (US); Christian Schopke, Carlsbad, CA (US); Noel Joy Sauer, Oceanside, CA (US); James Pearce, La Jolla, CA (US); Rosa E. Segami, Escondido, CA (US); Jerry Mozoruk, Encinitas, CA (US)

(73) Assignees: CIBUS US LLC, San Dieog, CA (US); CIBUS EUROPE B.V., Ad Kapelle (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/777,357

(22) PCT Filed: Mar. 14, 2014

(86) PCT No.: PCT/US2014/029566
§ 371 (c)(1),
(2) Date: Sep. 15, 2015

(87) PCT Pub. No.: WO2014/144951
PCT Pub. Date: Sep. 18, 2014

(65) Prior Publication Data
US 2016/0289691 A1    Oct. 6, 2016

Related U.S. Application Data

(60) Provisional application No. 61/801,333, filed on Mar. 15, 2013.

(51) Int. Cl.
*C12N 15/82*    (2006.01)
*C12N 9/22*    (2006.01)

(52) U.S. Cl.
CPC ........... *C12N 15/8213* (2013.01); *C12N 9/22* (2013.01); *C12N 2800/80* (2013.01)

(58) Field of Classification Search
None
See application file for complete search history.

(56) References Cited

U.S. PATENT DOCUMENTS 4,683,195 A    7/1987    Mullis et al.
4,683,202 A    7/1987    Mullis
(Continued)

FOREIGN PATENT DOCUMENTS

EP    0629387 A1    12/1994
EP    0679657 A2    11/1995
(Continued)

OTHER PUBLICATIONS

Chen et al. High-frequency genome editing using ssDNA oligonucleotides with zinc-finger nucleases. Nat Methods. Jul. 17, 2011;8(9):753-5.*

(Continued)

*Primary Examiner* — Cynthia E Collins
(74) *Attorney, Agent, or Firm* — Acuity Law Group, P.C.; Michael A. Whittaker

(57) ABSTRACT

The invention provides to improved methods for the modification of genes in plant cells, and plants and seeds derived therefrom. More specifically, the invention relates to the increased efficiency of targeted gene mutation by combining (Continued)

gene repair oligonucleotides with approaches that enhance the availability of components of the target cell gene repair mechanisms.

12 Claims, 4 Drawing Sheets

Specification includes a Sequence Listing.

(56) References Cited

U.S. PATENT DOCUMENTS

| | | | |
|---|---|---|---|
| 4,873,191 | A | 10/1989 | Wagner et al. |
| 4,945,050 | A | 7/1990 | Sanford et al. |
| 5,008,200 | A | 4/1991 | Ranch et al. |
| 5,024,944 | A | 6/1991 | Collins et al. |
| 5,100,792 | A | 3/1992 | Sanford et al. |
| 5,204,253 | A | 4/1993 | Sanford et al. |
| 5,219,746 | A | 6/1993 | Brinegar et al. |
| 5,268,463 | A | 12/1993 | Jefferson |
| 5,302,523 | A | 4/1994 | Coffee et al. |
| 5,334,711 | A | 8/1994 | Sproat et al. |
| 5,380,831 | A | 1/1995 | Adang et al. |
| 5,399,680 | A | 3/1995 | Zhu et al. |
| 5,424,412 | A | 6/1995 | Brown et al. |
| 5,436,391 | A | 7/1995 | Fujimoto et al. |
| 5,466,785 | A | 11/1995 | De Framond |
| 5,569,597 | A | 10/1996 | Grimsley et al. |
| 5,593,874 | A | 1/1997 | Brown et al. |
| 5,604,121 | A | 2/1997 | Hilder et al. |
| 5,608,142 | A | 3/1997 | Barton et al. |
| 5,608,144 | A | 3/1997 | Baden et al. |
| 5,608,149 | A | 3/1997 | Barry et al. |
| 5,659,026 | A | 8/1997 | Baszczynski et al. |
| 5,756,325 | A | 5/1998 | Kmiec |
| 5,760,012 | A | 6/1998 | Kmiec et al. |
| 5,780,296 | A | 7/1998 | Holloman et al. |
| 5,795,972 | A | 8/1998 | Kmiec |
| 5,871,984 | A | 2/1999 | Kmiec |
| 5,888,983 | A | 3/1999 | Kmiec et al. |
| 5,945,339 | A | 8/1999 | Holloman et al. |
| 5,962,426 | A | 10/1999 | Glazer |
| 5,986,053 | A | 11/1999 | Ecker et al. |
| 6,004,804 | A | 12/1999 | Kumar et al. |
| 6,010,907 | A | 1/2000 | Kmiec et al. |
| 6,072,050 | A | 6/2000 | Bowen et al. |
| 6,177,611 | B1 | 1/2001 | Rice |
| 6,271,360 | B1 | 8/2001 | Metz et al. |
| 6,479,292 | B1 | 11/2002 | Metz et al. |
| 6,753,458 | B1 | 6/2004 | Filho et al. |
| 7,060,500 | B2 | 6/2006 | Metz et al. |
| 9,512,444 | B2 * | 12/2016 | Chen .............. C12N 15/85 |
| 2003/0115641 | A1 | 6/2003 | Dobres et al. |
| 2009/0205064 | A1 * | 8/2009 | Schopke .......... C12N 15/8274 800/260 |
| 2011/0124072 | A1 | 5/2011 | Walker et al. |
| 2012/0122223 | A1 | 5/2012 | Gocal et al. |
| 2012/0178628 | A1 | 7/2012 | Schopke et al. |
| 2014/0298547 | A1 | 10/2014 | Sastry-Dent et al. |

FOREIGN PATENT DOCUMENTS

| | | |
|---|---|---|
| JP | 2010539986 A | 12/2010 |
| JP | 2010539986T A | 12/2010 |
| WO | 9849350 A1 | 11/1998 |
| WO | 9907865 A1 | 2/1999 |
| WO | 9940789 A1 | 8/1999 |
| WO | 9943838 A1 | 9/1999 |
| WO | 9958702 A1 | 11/1999 |
| WO | 9958723 A1 | 11/1999 |
| WO | 01025460 A2 | 4/2001 |
| WO | 2007073149 A1 | 6/2007 |
| WO | 2008148223 A1 | 12/2008 |
| WO | 2011117249 A1 | 9/2011 |
| WO | 2012012738 A1 | 1/2012 |

OTHER PUBLICATIONS

Zhang et al. High frequency targeted mutagenesis in *Arabidopsis thaliana* using zinc finger nucleases. Proc Natl Acad Sci U S A. Jun. 29, 2010;107(26):12028-33. Epub May 27, 2010.*

An et al., Transformation of Tobacco, Tomato, Potato, and *Arabidopsis thaliana* Using a Binary Ti Vector System. Plant Physiol. May 1986;81(1):301-305.

Archer and Keegstra, Current Views on Chloroplast Protein Import and Hypotheses on the Origin of the Transport Mechanism. J Bioenerg Biomembr. Dec. 1990;22(6):789-810.

Arimondo et al., Recognition and Cleavage of DNA by Rebeccamycin- or Benzopyridoquinoxaline Conjugated of Triple Helix-Forming Oligonucleotides. Bioorg Med Chem. Apr. 2000;8(4):777-784

Asano and Ugaki, Transgenic plants of Agrostis alba obtained by electroporation-mediated direct gene transfer into protoplasts. Plant Cell Rep. Feb. 1994;13(5):243-246.

Ayres and Park, Genetic Transformation of Rice. Crit Rev Plant Sci 13:219-239.

Ballas et al., Efficient functioning of plant promoters and poly(A) sites in Xenopus oocytes. Nucleic Acids Res. Oct. 11, 1989;17(19):7891-7903.

Barcelo et al., Transgenic cereal (tritordeum) plants obtained at high efficiency by microprojectile bombardment of inflorescence tissue. Plant J. Apr. 1994;5(4):583-592.

Barsby et al., A rapid and efficient alternative procedure for the regeneration of plants from hypocotyl protoplasts of *Brassica napus*. Plant Cell Rep. Apr. 1986;5(2):101-103.

Becker, et al., Fertile transgenic wheat from microprojectile bombardment of scutellar tissue. Plant J. Feb. 1994;5(2):299-307.

Belousov et al., Sequence-specific targeting and covalent modification of human genomic DNA. Nucleic Acids Res. Sep. 1, 1997;25(17):3440-3444.

Bendinskas et al., Sequence-Specific Photomodification of DNA by an Oligonucleotide-Phenanthrodihydrodioxin Conjugate. Bioconjug Chem. Sep.-Oct. 1998;9(5):555-563.

Borkowska et al., Transformation of diploid potato with an Agrobacterium tumefaciens binary vector system: I. Methodological approach. Acta Physiol Plant. 1994;16(3):225-230.

Callis et al., Introns increase gene expression in cultured maize cells. Genes Dev. Dec. 1987;1(10):1183-1200.

Campbell and Gowri, Codon Usage in Higher Plants, Green Algae, and Cyanobacteria. Plant Physiol. Jan. 1990;92(1):1-11.

Canevascini et al., Tissue-Specific Expression and Promoter Analysis of the Tobacco ltp1 Gene. Plant Physiol. Oct. 1996;112(2):513-524.

Capeechi et al., Altering the Genome by Homologous Recombination. Science. Jun. 16, 1989;244(4910):1288-1292.

Casas et al., Transgenic sorghum plants via microprojectile bombardment. Proc Natl Acad Sci U S A. Dec. 1, 1993;90(23):11212-11216.

Cermak et al., Efficient design and assembly of custom TALEN and other TAL effector-based constructs for DNA targeting. Nucleic Acids Res. Jul. 2011;39(12):e82 (11 pages).

Chan et al., Targeted Correction of an Episomal Gene in Mammalian Cells by a Short DNA Fragment Tethered to a Triplex-forming Oligonucleotide. J Biol Chem. Apr. 23, 1999;274(17)11541-11548.

Chee and Slightom, Transformation of cucumber tissues by microprojectile bombardment: identification of plants containing functional and non-functional transferred genes. Gene. Sep. 10, 1992;118(2):255-260.

Christensen and Quail, Sequence analysis and transcriptional regulation by heat shock of polyubiquitin transcripts from maize. Plant Mol Biol. Jun. 1989;12(6):619-632.

Christensen et al., Maize polyubiquitin genes: structure, thermal perturbation of expression and transcript splicing, and promoter activity following transfer to protoplasts by electroporation. Plant Mol Biol. Feb. 1992;18(4):675-689.

Christou et al., The development of a variety-independent gene-transfer method for rice. Trends Biotechnol. 1992;10:239-246.

(56) References Cited

OTHER PUBLICATIONS

Christou, Genetic engineering of crop legumes and cereals: current status and recent advances. Agro Food Ind Hi Tech. Mar.-Apr. 1994;5:17-27.
Christou, Philosophy and Practice of Variety-Independent Gene Transfer into Recalcitrant Crops. In Vitro Cell Dev Biol—Plant 1993;29:119-124.
Chuong et al., A simple culture method for *Brassica* hypototyl protoplasts. Plant Cell Rep. Feb. 1985;4(1):4-6.
Clark et al., Mutations at the Transit Peptide-Mature Protein Junction Separate Two Cleavage Events During Chloroplast Import of the Chlorophyll a/b-Binding Protein. J Biol Chem. Oct. 15, 1989;264(29):17544-17550.
Clough and Bent, Floral dip: a simplified method for Agrobacterium-mediated transformation of *Arabidopsis thaliana*. Plant J. Dec. 1998;16(6):735-43.
Columbier et al., Interstrand cross-linking reaction in triplexes containing a monofunctional transplatin-adduct. Nucleic Acids Res. Nov. 15, 1996;24(22):4519-4524.
Cong et al., Multiplex Genome Engineering Using CRISPR/Cas Systems. Science. Feb. 15, 2013;339(6121):819-823.
The Office Action issued by SIPO in PRC patent application No. 201480024688.5 dated Nov. 2, 2016—incl Eng lang transl.
Cousins et al., Transformation of an Australian Cotton Cultivar: Prospects for Cotton Improvement through Genetic Engineering. Aust J Plant Physiol. 1991;18:481-494.
Davies et al., Transformation of peas. Plant Cell Rep. Jan. 1993;12(3):180-183.
De Block, Genotype-independent leaf disc transformation of potato (*Solanum tuberosum*) using Agrobacterium tumefaciens. Theor Appl Genet. Nov. 1988;76(5):767-774.
de Castro Silva Filho et al., Mitochondrial and chloroplast targeting sequences in tandem modify protein import specificity in plant organelles. Plant Mol Biol. Feb. 1996;30(4):769-780.
Della-Cioppa et al. Protein Trafficking in Plant Cells. Plant Physiol. Aug. 1987;84(4):965-968.
Dervan and Bürli, Sequence-specific DNA recognition by polyamides. Curr Opin Chem Biol. Dec. 1999;3(6):688-693.
D'Halluin et al., Transformation of Sugarbeet (*Beta vulgaris* L.) and Evaluation of Herbicide Resistance in Transgenic Plants. Bio/Technol. Mar. 1992;10:309-314.
Dhir et al., Regeneration of fertile plants from protoplasts of soybean (*Glycine max* L. Merr.): genotypic differences in culture response. Plant Cell Rep. Jun. 1992;11(5-6):285-289.
Dhir et al., Regeneration of Transgenic Soybean (*Glycine max*) Plants from Electroporated Protoplasts. Plant Physiol. May 1992:99(1):81-88.
Dicarlo et al., Genome engineering in *Saccharomyces cerevisiae* using CRISPR-Cas systems. Nucleic Acids Res. Apr. 2013;41(7):4336-4343.
Dong and McHughen, Transgenic flax plants from Agrobacterium mediated transformation: incidence of chimeric regenerants and inheritance of transgenic plants. Plant Sci. 1993;91:139-148.
Eapen and George, Agrobacterium tumefaciens mediated gene transfer in peanut (*Arachis hypogaea* L.). Plant Cell Rep. Jul. 1994;13(10):582-586.
Eudes and Chugh, Cell-penetrating peptides: From mammalian to plant cells. Plant Signal Behay. Aug. 2008;3(8):549-550.
Faruqi et al., Recombination Induced by Triple-Helix-Targeted DNA Damage in Mammalian Cells. Mol Cell Biol. Dec. 1996;16(12):6820-6828.
Folger et al., Patterns of Integration of DNA Microinjected into Cultured Mammalian Cells: Evidence for Homologous Recombination Between Injected Plasmid DNA Molecules. Mol Cell Biol. Nov. 1982;2(11):1372-1387.
Fry et al., Transformation of *Brassica* napus with Agrobacterium tumefaciens based vectors. Plant Cell Rep. Oct. 1987;6(5):321-325.
Fujiwara and Kato, Split luciferase complementation assay to study protein-protein interactions in *Arabidopsis* protoplasts. Plant J. Oct. 2007;52(1):185-195.
Gallie and Young, The Regulation of Gene Expression in Transformed Maize Aleurone and Endosperm Protoplasts. Analysis of Promoter Activity, Intron Enhancement, and Mrna Untranslated Regions on Expression. Plant Physiol. Nov. 1994;106(3):929-939.
Gallie et al., A comparison of eukaryotic viral 5'-leader sequences as enhancers of mRNA expression in vivo. Nucleic Acids Res. Nov. 11, 1987;15(21):8693-8711.
Rubnitz and Subramani, The Minimum Amount of Homology Required for Homologous Recombination in Mammalian Cells. Mol Cell Biol. Nov. 1984;4(11):2253-2258.
Russell and Fromm, Tissue-specific expression in transgenic maize of four endosperm promoters from maize and rice. Transgenic Res. Mar. 1997;6(2):157-168.
Sanfacon et al., A dissection of the cauliflower mosaic virus polyadenylation signal. Genes Dev. Jan. 1991;5(1):141-149.
Schmidt et al., A Novel Operon Organization Involving the Genes for Chorismate Synthase (Aromatic Biosynthesis Pathway) and Ribosomal GTPase Center Proteins (LII, LI, LIO, L12: rpIKAJL) in Cyanobacterium Synechocystis PCC 6803. J Biol Chem. Dec. 25, 1993;268(36):27447-27457.
Schnell et al., Signal Peptide Analogs Derived from Two Chloroplast Precursors Interact with the Signal Recognition System of the Chloroplast Envelope. J Biol Chem. Feb. 15, 1991;266(5):3335-3342.
Segal and Carroll, Endonuclease-induced, targeted homologous extrachromosomal recombination in Xenopus oocytes. Proc Natl Acad Sci U S A. Jan. 31, 1995;92(3):806-810.
Senaratna et al., Desiccation of microspore derived embryos of oilseed rape (*Brassica napus* L.). Plant Cell Rep. Sep. 1991:10(6-7):342-344.
Sergeyev et al., Catalytic site-specific cleavage of a DNA-target by an oligonucleotide carrying bleomycin A5. Nucleic Acids Res. Nov. 11, 1995:23(21):4400-4406.
Shah et al., Engineering Herbicide Tolerance in Transgenic Plants. Science. Jul. 25, 1986;233(4762):478-481.
Shetty et al., Stimulation of in vitro shoot organogenesis in Glycine max(Merrill.) by allantoin and amides. Plant Science 1992;81:245-251.
Skuzeski et al., Analysis of leaky viral translation termination codons in vivo by transient expression of improved beta-glucuronidase vectors. Plant Mol Biol. Jul. 1990;15(1):65-79.
Sommer et al., Reporter System for the Detection of In Vivo Gene Conversion: Changing Colors From Blue to Green Using GFP Variants. Mol Biotechnol. Jun. 2006;33(2):115-122.
Sone et al., A Novel Gene Delivery System in Plants with Calcium Alginate Micro-Beads. J Biosci Bioeng. 2002;94(1):87-91.
Staub and Maliga, Accumulation of D1 polypeptide in tobacco plastids is regulated via the untranslated region of the psbA mRNA. EMBO J. Feb. 1993;12(2):601-606.
Stephens et al., Agronomic evaluation of tissue-culture-derived soybean plants. Theor Appl Genet. Oct. 1991;82(5):633-635.
Svab and Maliga, High-frequency plastid transformation in tobacco by selection for a chimeric aadA gene. Proc Natl Acad Sci U S A. Feb. 1, 1993;90(3):913-917.
Svab et al., Stable transformation of plastids in higher plants. Proc Natl Acad Sci U S A. Nov. 1990;87(21):8526-8530.
Swanson, Microspore Culture in *Brassica*. Methods Mol Biol. 1990;6:159-69.
Takasugi et al., Sequence-specific photo-induced cross-linking of the two strands of double-helical DNA by a psoralen covalently linked to a triple helix-forming oligonucleotide. Proc Natl Acad Sci U S A. Jul. 1, 1991;88(13):5602-5606.
Takeshita et al., Oligodeoxynucleotides Containing Synthetic Abasic Sites. Model Substrates for DNA Polymerases and Apurinic/Apyrimidinic Endonucleases. J Biol Chem. Jul. 25, 1987;262(21):10171-10179.
Torney et al., Mesoporous Silica Nanoparticles Deliver DNA and Chemicals into Plants, Nature Nanotechnol. May 2007:2:295-300.
Topfer et al., Uptake and Transient Expression of Chimeric Genes in Seed-Derived Embryos. Plant Cell. Jan. 1989;1(1):133-139.
Van Camp et al., Tissue-Specific Activity of Two Manganese Superoxide Dismutase Promoters in Transgenic Tobacco. Plant Physiol. Oct. 1996;112(2):525-535.

(56) References Cited

OTHER PUBLICATIONS

Velten et al., Isolation of a dual plant promoter fragment from the Ti plasmid of Agrobacterium tumefaciens. EMBO J. Dec. 1, 1984;3(12):2723-2730.
von Heijne et al., CHLPEP-A Database of Chloroplast Transit Peptides. Plant Mol Biol Rep. 1991;9(2):104-126.
Wan and Lemaux, Generation of Large Numbers of Independently Transformed Fertile Barley Plants. Plant Physiol. Jan. 1994;104(1):37-48.
Wang et al., Carcinogens Can Induce Homologous Recombination between Duplicated Chromosomal Sequences in Mouse L Cells. Mol Cell Biol. Jan. 1988;8(1):196-202.
Wang et al., Hairpin RNAs derived from RNA polymerase II and polymerase III promoter-directed transgenes are processed differently in plants. RNA. May 2008;14(5):903-913.
Wang et al., Mutagenesis in Mammalian Cells Induced by Triple Helix Formation and Transcription-Coupled Repair. Science. Feb. 9, 1996;271(5250):802-805.
Wang et al., Targeted Mutagenesis in Mammalian Cells Mediated by Intracellular Triple Helix Formation. Mol Cell Biol. Mar. 1995;15(3):1759-1768.
Wong and Capecchi, Homologous Recombination between Coinjected DNA Sequences Peaks in Early to Mid-S Phase. Mol Cell Biol. Jun. 1987;7(6):2294-2295.
Yamamoto et al., Light-responsive elements of the tobacco PSI-D gene are located both upstream and within the transcribed region. Plant J. Aug. 1997;12(2):255-265.
Yamamoto et al., The Promoter of a Pine Photosynthetic Gene Allows Expression of a β-Glucuronidase Reporter Gene in Transgenic Rice Plants in a Light-Independent but Tissue-Specific Manner. Plant Cell Physiol. Jul. 1994;35(5):773-778.
Zhang et al., Transcription Activator-Like Effector Nucleases Enable Efficient Plant Genome Engineering 1[W][OA]. Plant Physiol. Jan. 2013;161(1):20-27.
Zhao and Last, Immunological Characterization and Chloroplast Localization of the Tryptophan Biosynthetic Enzymes of the Flowering Plant *Arabidopsis thaliana*. J Biol Chem. Mar. 17, 1995;270(11):6081-6087.
Beetham et al., A tool for functional plant genomics: Chimeric RNA/DNA oligonucleotides cause in vivo gene-specific mutations. Proc Natl Acad Sci U S A. Jul. 20, 1999;96(15):8774-8778.
Bonner and Kmiec, DNA breakage associated with targeted gene alteration directed by DNA oligonucleotides. Mutat Res. Oct. 2, 2009;669(1-2):85-94.
The Partial Supplementary European Search Report issued in EP 14764596 dated Aug. 30, 2016.
Jinek et al., A Programmable Dual-RNA-Guided DNA Endonuclease in Adaptive Bacterial Immunity. Science. Aug. 17, 2012;337(6096):816-821.
Rice et al., Genetic Repair of Mutations in Plant Cell-Free Extracts Directed by Specific Chimeric Oligonucleotides. Plant Physiol. Jun. 2000;123(2):427-437.
Gallois et al., Electroporation of Tobacco Leaf Protoplasts Using Plasmid DNA or Total Genomic DNA. Methods Mol Biol. 1995;55:89-107.
Glen Research, Technical Brief—Preparation of Oligonucleotides Containing Abasic Sites. Accessed online at: http://www.glenresearch.com/GlenReports/GR21-14.html (1 page), originally published in Glen Report 14.1 (2001).
Guerineau et al., Effect of deletions in the cauliflower mosaic virus polyadenylation sequence on the choice of the polyadenylation sites in tobacco protoplasts. Mol Gen Genet. Apr. 1991;226(1-2):141-144.
Guevara-Garcia et al., Tissue-specific and wound-inducible pattern of expression of the mannopine synthase promoter is determined by the interaction between positive and negative cis-regulatory elements. Plant J. Sep. 1993;4(3):495-505.
Guo, Transgenic Plants Obtained From Wheat Protoplasts Transformed by PEG-mediated Direct Gene Transfer. Chin Sci. Bull. Dec. 1993;38(24):2072-2078.
Hansen et al., Wound-inducible and organ-specific expression of ORF13 from Agrobacterium rhizogenes 8196 T-DNA in transgenic tobacco plants. Mol Gen Genet. Apr. 16, 1997;254(3):337-343.
Hanson and Sedivy, Analysis of Biological Selections for High-Efficiency Gene Targeting. Mol Cell Biol. Jan. 1995;15(1):45-51.
Hartman et al., Herbicide Resistant Turf grass (*Agrostis palustris* Huds.) by Biolistic Transformation. Nature BioTechnol. 1994;12:919-923.
Havre and Glazer, Targeted Mutagenesis of Simian Virus 40 DNA Mediated by a Triple Helix-Forming Oligonucleotide. J Virol. Dec. 1993;67(12):7324-7331.
Havre et al., Targeted mutagenesis of DNA using triple helix-forming oligonucleotides linked to psoralen. Proc Natl Acad Sci U S A. Aug. 15, 1993;90(16):7879-7883.
He et al., A simplified system for generating recombinant adenoviruses. Proc Natl Acad Sci U S A. Mar. 3, 1998;95(5):2509-2514.
Joshi et al., Putative polyadenylation signals in nuclear genes of higher plants: a compilation and analysis. Nucleic Acids Res. Dec. 10, 1987;15(23):9627-9640.
Kane et al., Specific Cleavage of a DNA Triple Helix by FenII-Bleomycin. Biochemistry. Dec. 26, 1995;34(51):16715-24.
Kartha et al., In vitro Plant Formation from Stem Explants of Rape (*Brassica napus* cv. Zephyr). Physiol. Plant, 1974;31:217-220.
Kawamata et al., Temporal and Spatial Pattern of Expression of the Pea Phenylalanine Ammonia-Lyase Gene 1 Promoter in Transgenic Tobacco. Plant Cell Physiol. Jul. 1997;38(7):792-803.
Kim et al., DNA. RNA heteroduplex containing 8-oxo-7,8-dihydroguanosine: base pairing, structures, and thermodynamic stability. J Biochem Mol Biol. Nov. 30, 2004;37(6):657-662.
Kim et al., Hybrid restriction enzymes: zinc finger fusions to Fok I cleavage domain. Proc Natl Acad Sci U S A. Feb. 6, 1996;93(3):1156-1160.
Kipp et al., Gene Targeting in Plants via Site-Directed Mutagenesis. Methods Mol Biol. 2000;133:213-221.
Komatsuda et al., Genotype X Sucrose Interactions for Somatic Embryogenesis in Soybeans. Crop Sci. 1991;31(2):333-337.
Komatsuda et al., Maturation and germination of somatic embryos as affected by sucrose and plant growth regulators in soybeans *Glycine gracilis* Skvortz and *Glycine max* (L.) Merr. Plant Cell, Tissue and Organ Culture, 1992;28(1):103-113.
Kunzelmann et al., Gene targeting of CFTR DNA in CF epithelial cells. Gene Ther. Oct. 1996;3(10):859-867.
Lam, Analysis of Tissue-Specific Elements in the Camv 35S Promoter. Results Probl Cell Differ. 1994;20:181-196.
Lamppa et al., The Chlorophyll a/b-binding Protein Inserts into the Thylakoids Independent of Its Cognate Transit Peptide. J Biol Chem. Oct. 15, 1988;263(29):14996-14999.
Landgraf et al., Oligonucleotide-Directed Nucleic Acid Scission by Micrococcal Nuclease. Sep. 6, 1994;33(35):10607-10615.
Last et al., pEmu: an improved promoter for gene expression in cereal cells. Theor Appl Genet. May 1991;81(5):581-588.
Lawrence and Kindle, Alterations in the Chlamydomonas Plastocyanin Transit.
Lukhtanov et al., Minor Groove DNA Alkylation Directed by Major Groove Triplex Forming Oligodeoxyribonucleotides. Nucleic Acids Res. Dec. 15, 1997;25(24):5077-5084.
Maniatis et al., Regulation of Inducible and Tissue-Specific Gene Expression. Science. Jun. 5, 1987;236(4806):1237-1245.
Mathur et al., A simple method for isolation, fiquid culture, transformation and regeneration of *Arabidopsis thaliana* protoplasts. Plant Cell Rep. Jan. 1995;14(4):221-226.
Matsuoka et al., Tissue-specific light-regulated expression directed by the promoter of a C4 gene, maize pyruvate, orthophosphate dikinase, in a C3 plant, rice. Proc Natl Acad Sci U S A. Oct. 15, 1993;90(20):9586-9590.
McBride et al., Controlled expression of plastid transgenes in plants based on a nuclear DNA-encoded and plastid-targeted T7 RNA polymerase. Proc Natl Acad Sci U S A. Jul. 19, 1994;91(15):7301-7305.
McElroy et al., Isolation of an Efficient Actin Promoter for Use in Rice Transformation. Plant Cell. Feb. 1990;2(2):163-171.

(56) References Cited

OTHER PUBLICATIONS

Mogen et al., Upstream Sequences Other than AAUAAA Are Required for Efficient Messenger RNA 3'-End Formation in Plants. Plant Cell. Dec. 1990;2(12):1261-1272.

Morlan et al., Mutation Detection by Real-Time PCR: A Simple, Robust and Highly Selective Method. PLoS One. 2009;4(2):e4584 (11 pages).

Moser and Dervan, Sequence-Specific Cleavage of Double Helical DNA by Triple Helix Formation. Science. Oct. 30, 1987;238(4827):645-650.

Munroe and Jacobson, Tales of poly(A): a review. Gene. Jul. 16, 1990;91(2):151-158.

Murray et al., Codon usage in plant genes. Nucleic Acids Res. Jan. 25, 1989;17(2):477-498.

Narasimhulu and Chopra, Species specific shoot regeneration response of cotyledonary explants of *Brassicas*. Plant Cell Rep. Mar. 1988;7(2):104-106.

Nunez et al., Long-Range Guanine Oxidation in DNA Restriction Fragments by a Triplex-Directed Naphthalene Diimide Intercalator. Biochemistry. May 23, 2000;39(20):6190-6199.

Odell et al., Identification of DNA sequences required for activity of the cauliflower mosaic virus 35S promoter. Nature Feb. 28, 1985;313:810-812.

Oh et al., Triple helix-forming oligonucleotides target psoralen adducts to specific chromosomal sequences in human cells. Nucleic Acids Res. Dec. 15, 1999;27(24):4734-4742.

Orozco and Ogren, Localization of light-inducible and tissue-specific regions of the spinach ribulose bisphosphate carboxylase/oxygenase (rubisco) activase promoter in transgenic tobacco plants. Plant Mol Biol. Dec. 1993;23(6):1129-1138.

Pandey et al., Plant Regeneration from Leaf and Hypocotyl Explants of Glycine wightii (W. and A.) VERDC. var. *longicauda*. Japan J. Breed. 1992;42:1-5.

Pei et al., Site-specific cleavage of duplex DNA by a semisynthetic nuclease via triple-helix formation. Proc Natl Acad Sci U S A. Dec. 1990;87(24):9858-9862.

Pilch et al., The Thermodynamics of Polyamide—DNA Recognition: Hairpin Polyamide Binding in the Minor Groove of Duplex DNA. Biochemistry. Feb. 16, 1999;38(7):2143-2151.

Posvic et al., Sequence-Specific Alkylation of Double-Helical DNA by Oligonucleotide-Directed Triple-Helix Formation. J Am Chem Soc 1990;112:9428-9430.

Proudfoot, Poly(A) Signals. Cell. Feb. 22, 1991;64(4):671-674.

Rinehart et al., Tissue-Specific and Developmental Regulation of Cotton.

Romer et al., Expression of the genes encoding the early carotenoid biosynthetic enzymes in Capsicum annuum. Biochem Biophys Res Commun. Nov. 15, 1993;196(3):1414-1421.

Rouet et al., Expression of a site-specific endonuclease stimulates homologous recombination in mammalian cells. Proc Natl Acad Sci U S A. Jun. 21, 1994;91(13):6064-6068.

The International Search Report and Written Opinion dated Aug. 21, 2014 in PCT/US2014/029566 (9 pages).

Non-Final Office Action issued by the USPTO in U.S. Appl. No. 15/069,885 dated May 30, 2017.

Majlessi et al., Advantages of 2'-O-methyl oligoribonucleotide probes for detecting RNA targets. Nucleic Acids Res. May 1, 1998;26(9):2224-2229.

The office action issued by EPO in European patent application No. 14764596.4 dated Sep. 26, 2017.

Declaration of Dr. Noel Joy Sauer executed Aug. 30, 2017, filed in U.S. Appl. No. 15/069,885, Inventors Peter R. Beetham et al. (14 pages).

The office action issued by the JPO in Japanese patent application No. 2016-503142 dated Sep. 18, 2018—incl Engl lang transl (8 pages total).

Hwang et al., Efficient genome editing in zebrafish using a CRISPR-Cas system. Nat Biotechnol. Mar. 2013; 31(3):227-229.

\* cited by examiner

FIG. 2

A. Okasaki Fragment GRONs (BFP4 or 0/C or NC/71/5' 2'-O-Me (1))

BFP4/NC: U UCA UGU GGU CGG GGT AGC GGT TGA AGC ACT GCA CGC CGT AGG TGA AGG TGG TCA CGA GGG TGG GCC AGG G (71-mer)

BFP0/NC: U UCA UGU GGU CGG GGT AGC GGT TGA AGC ACT GCA CGC CGT GGG TGA AGG TGG TCA CGA GGG TGG GCC AGG G (71-mer)

BFP4/C: G CUG CCC GUG CCC TGG CCC ACC CTC GTG ACC ACC TTC ACC TAC GGC GTG CAG TGC TTC AGC CGC TAC CCC G (71-mer)

BFP0/C: G CUG CCC GUG CCC TGG CCC ACC CTC GTG ACC ACC TTC ACC CAC GGC GTG CAG TGC TTC AGC CGC TAC CCC G (71-mer)

RNA bases

2'-O-Me group on all of the RNA bases except for the base closest to the first DNA base of the GRON
(RNA base without the 2'-O-Me group is in green)

B. Okasaki Fragment GRONs (BFP4 or 0/C or NC/71/5' 2'-O-Me (9))

BFP4/NC: U UCA UGU GGU CGG GGT AGC GGT TGA AGC ACT GCA CGC CGT AGG TGA AGG TGG TCA CGA GGG TGG GCC AGG G (71-mer)

BFP0/NC: U UCA UGU GGU CGG GGT AGC GGT TGA AGC ACT GCA CGC CGT GGG TGA AGG TGG TCA CGA GGG TGG GCC AGG G (71-mer)

BFP4/C: G CUG CCC GUG CCC TGG CCC ACC CTC GTG ACC ACC TTC ACC TAC GGC GTG CAG TGC TTC AGC CGC TAC CCC G (71-mer)

BFP0/C: G CUG CCC GUG CCC TGG CCC ACC CTC GTG ACC ACC TTC ACC CAC GGC GTG CAG TGC TTC AGC CGC TAC CCC G (71-mer)

RNA bases

2'-O-Me group on all of the RNA bases except for the base closest to the first DNA base of the GRON
(RNA base without the 2'-O-Me group is in green)

FIG. 3

METHODS AND COMPOSITIONS FOR INCREASING EFFICIENCY OF TARGETED GENE MODIFICATION USING OLIGONUCLEOTIDE-MEDIATED GENE REPAIR

The present invention is filed under 35 U.S.C. § 371 as the U.S. national phase of International Application No. PCT/US2014/029566, filed Mar. 14, 2014, which designated the United States and claims priority to U.S. Provisional Patent Application 61/801,333 filed Mar. 15, 2013, each of which is hereby incorporated by reference in its entirety including all tables, figures, and claims.

SEQUENCE LISTING

This application includes an electronically submitted sequence listing in .txt format. The .txt file contains a sequence listing entitled "2016-05-04 CIBUS-024-US_ST25.txt" created on May 4, 2016 and is 15,525 bytes in size. The sequence listing contained in this .txt file is part of the specification and is hereby incorporated by reference herein in its entirety.

FIELD OF THE INVENTION

This invention generally relates to novel methods to improve the efficiency of the targeting of modifications to specific locations in genomic or other nucleotide sequences. Additionally, this invention relates to target DNA that has been modified, mutated or marked by the approaches disclosed herein. The invention also relates to cells, tissue, and organisms which have been modified by the invention's methods.

BACKGROUND OF THE INVENTION

The following discussion of the background of the invention is merely provided to aid the reader in understanding the invention and is not admitted to describe or constitute prior art to the present invention.

The modification of genomic DNA is central to advances in biotechnology, in general, and biotechnologically based medical advances, in particular. Efficient methods for site-directed genomic modifications are desirable for research and possibly for gene therapy applications. One approach utilizes triplex-forming oligonucleotides (TFO) which bind as third strands to duplex DNA in a sequence-specific manner, to mediate directed mutagenesis. Such TFO can act either by delivering a tethered mutagen, such as psoralen or chlorambucil (Havre et al., Proc Nat'l Acad Sci, U.S.A. 90:7879-7883, 1993; Havre et al., J Virol 67:7323-7331, 1993; Wang et al., Mol Cell Biol 15:1759-1768, 1995; Takasugi et al., Proc Nat'l Acad Sci, U.S.A. 88:5602-5606, 1991; Belousov et al., Nucleic Acids Res 25:3440-3444, 1997), or by binding with sufficient affinity to provoke error-prone repair (Wang et al., Science 271:802-805, 1996).

Another strategy for genomic modification involves the induction of homologous recombination between an exogenous DNA fragment and the targeted gene. This approach has been used successfully to target and disrupt selected genes in mammalian cells and has enabled the production of transgenic mice carrying specific gene knockouts (Capechi et al., Science 244:1288-1292, 1989; U.S. Pat. No. 4,873,191 to Wagner). This approach, however, relies on the transfer of selectable markers to allow isolation of the desired recombinants. Without selection, the ratio of homologous to non-homologous integration of transfected DNA in typical gene transfer experiments is low, usually in the range of 1:1000 or less (Sedivy et al., Gene Targeting, W. H. Freeman and Co., New York, 1992). This low efficiency of homologous integration limits the utility of gene transfer for experimental use or gene therapy. The frequency of homologous recombination can be enhanced by damage to the target site from UV irradiation and selected carcinogens (Wang et al., Mol Cell Biol 8:196-202, 1988) as well as by site-specific endonucleases (Sedivy et al, Gene Targeting, W. H. Freeman and Co., New York, 1992; Rouet et al., Proc Nat'l Acad Sci, U.S.A. 91:6064-6068, 1994; Segal et al., Proc Nat'l Acad Sci, U.S.A. 92:806-810, 1995). In addition, DNA damage induced by triplex-directed psoralen photoadducts can stimulate recombination within and between extrachromosomal vectors (Segal et al., Proc Nat'l Acad Sci, U.S.A. 92:806-810, 1995; Faruqi et al., Mol Cell Biol 16:6820-6828, 1996; U.S. Pat. No. 5,962,426 to Glazer).

Other work has helped to define parameters that influence recombination in mammalian cells. In general, linear donor fragments are more recombinogenic than their circular counterparts (Folger et al., Mol Cell Biol 2:1372-1387, 1982). Recombination is also influenced by the length of uninterrupted homology between both the donor and target sites, with short fragments appearing to be ineffective substrates for recombination (Rubnitz et al., Mol Cell Biol 4:2253-2258, 1984). Nonetheless, several recent efforts have focused on the use of short fragments of DNA or DNA/RNA hybrids for gene correction. (Kunzelmann et al., Gene Ther 3:859-867, 1996).

The sequence-specific binding properties of TFO have been used to deliver a series of different molecules to target sites in DNA. For example, a diagnostic method for examining triplex interactions utilized TFO coupled to Fe-EDTA, a DNA cleaving agent (Moser et al., Science 238:645-650, 1987). Others have linked biologically active enzymes like micrococcal nuclease and streptococcal nuclease to TFO and demonstrated site-specific cleavage of DNA (Pei et al., Proc Nat'l Acad Sci U.S.A. 87:9858-9862, 1990; Landgraf et al., Biochemistry 33:10607-10615, 1994). Furthermore, site-directed DNA damage and mutagenesis can be achieved using TFO conjugated to either psoralen (Havre et al., Proc Nat'l Acad Sci U.S.A. 90:7879-7883, 1993; Takasurgi et al., Proc Nat'l Acad Sci U.S.A. 88:5602-5606, 1991) or alkylating agents (Belousov et al., Nucleic Acids Res 25:3440-3444, 1997; Posvic et al., J Am Chem Soc 112:9428-9430, 1990).

WIPO Patent Application WO/2001/025460 describes methods for mutating a target DNA sequence of a plant that include the steps of (1) electroporating into a microspore of the plant a recombinagenic oligonucleobase that contains a first homologous region that has a sequence identical to the sequence of at least 6 base pairs of a first fragment of the target DNA sequence and a second homologous region which has a sequence identical to the sequence of at least 6 base pairs of a second fragment of the target DNA sequence, and an intervening region which contains at least 1 nucleobase heterologous to the target DNA sequence, which intervening region connects the first homologous region and the second homologous region; (2) culturing the microspore to produce an embryo; and (3) producing from the embryo a plant having a mutation located between the first and second fragments of the target DNA sequence, e. g., by culturing the microspore to produce a somatic embryo and regenerating the plant from the embryo. In various embodiments of the invention, the recombinagenic oligonucleobase is an MDON and each of the homologous regions contains an RNA segment of at least 6 RNA-type nucleotides; the intervening region is at least 3 nucleotides in length; the first and or second RNA segment contains at least 8 contiguous 2'-substituted ribonucleotides.

One of the major goals of biological research is the targeted modification of the genome. As noted above, although methods for delivery of genes into mammalian cells are well developed, the frequency of modification and/or homologous recombination is limited (Hanson et al., Mol Cell Biol 15:45-51 1995). As a result, the modification of genes is a time consuming process. Numerous methods have been contemplated or attempted to enhance modification and/or recombination between donor and genomic DNA. However, the present techniques often exhibit low rates of modification and/or recombination, or inconsistency in the modification and/or recombination rate, thereby hampering research and gene therapy technology.

SUMMARY OF THE INVENTION

The present invention provides novel methods and compositions for improving the efficiency of the targeting of modifications to specific locations in genomic or other nucleotide sequences. As described hereinafter, nucleic acids which direct specific changes to the genome may be combined with various approaches to enhance the availability of components of the natural repair systems present in the cells being targeted for modification.

In a first aspect, the invention relates to methods for introducing a gene repair oligonucleobase (GRON)-mediated mutation into a target deoxyribonucleic acid (DNA) sequence in a plant cell. The methods comprise, inter alia, culturing the plant cell under conditions that increase one or more cellular DNA repair processes prior to, and/or coincident with, delivery of a GRON into the plant cell; and/or delivery of a GRON into the plant cell greater than 55 bases in length, the GRON optionally comprising two or more mutation sites for introduction into the target DNA.

In certain embodiments, the conditions that increase one or more cellular DNA repair processes comprise one or more of: introduction of one or more sites into the GRON or into the plant cell DNA that are targets for base excision repair, introduction of one or more sites into the GRON or into the plant cell DNA that are targets for non-homologous end joining, introduction of one or more sites into the GRON or into the plant cell DNA that are targets for microhomology-mediated end joining, introduction of one or more sites into the GRON or into the plant cell DNA that are targets for homologous recombination, and introduction of one or more sites into the GRON or into the plant cell DNA that are targets for pushing repair.

As described hereinafter, GRONs for use in the present invention can comprises one or more of the following alterations from conventional RNA and DNA nucleotides:
one or more abasic nucleotides;
one or more 8'oxo dA and/or 8'oxo dG nucleotides;
a reverse base at the 3' end thereof;
one or more 2'O-methyl nucleotides;
one or more 2'O-methyl RNA nucleotides at the 5' end thereof, and preferably 2, 3, 4, 5, 6, 7, 8, 9, 10, or more;
an intercalating dye;
a 5' terminus cap;
a backbone modification selected from the group consisting of a phosphothioate modification, a methyl phosphonate modification, a locked nucleic acid (LNA) modification, a O-(2-methoxyethyl) (MOE) modification, a di PS modification, and a peptide nucleic acid (PNA) modification;
one or more intrastrand crosslinks;
one or more fluorescent dyes conjugated thereto, preferably at the 5' or 3' end of the GRON; and
one or more bases which increase hybridization energy. This list is not meant to be limiting.

As described hereinafter, in certain embodiments GRON quality and conversion efficiency may be improved by synthesizing all or a portion of the GRON using nucleotide multimers, such as dimers, trimers, tetramers, etc improving its purity.

In certain embodiments, the target deoxyribonucleic acid (DNA) sequence is within the plant cell genome. The plant cell may be non-transgenic or transgenic, and the target DNA sequence may be a transgene or an endogenous gene of the plant cell.

In certain embodiments, the conditions that increase one or more cellular DNA repair processes comprise introducing one or more compounds which induce single or double DNA strand breaks into the plant cell prior to or coincident with delivering the GRON into the plant cell. Exemplary compounds are described hereinafter.

The methods and compositions described herein are applicable to plants generally. By way of example only, a plant species may be selected from the group consisting of canola, sunflower, corn, tobacco, sugar beet, cotton, maize, wheat, barley, rice, alfafa, barley, sorghum, tomato, mango, peach, apple, pear, strawberry, banana, melon, potato, carrot, lettuce, onion, soy bean, soya spp, sugar cane, pea, chickpea, field pea, faba bean, lentils, turnip, rutabaga, brussel sprouts, lupin, cauliflower, kale, field beans, poplar, pine, *eucalyptus*, grape, citrus, triticale, alfalfa, rye, oats, turf and forage grasses, flax, oilseed rape, mustard, cucumber, morning glory, balsam, pepper, eggplant, marigold, lotus, cabbage, daisy, carnation, tulip, iris, and lily. These may also apply in whole or in part to all other biological systems including but not limited to bacteria, fungi and mammalian cells and even their organelles (e.g., mitochondria and chloroplasts).

In certain embodiments, the methods further comprise regenerating a plant having a mutation introduced by the GRON from the plant cell, and may comprise collecting seeds from the plant.

In related aspects, the present invention relates to plant cells comprising a genomic modification introduced by a GRON according to the methods described herein, a plant comprising a genomic modification introduced by a GRON according to the methods described herein, or a seed comprising a genomic modification introduced by a GRON according to the methods described herein.

Other embodiments of the invention will be apparent from the following detailed description, exemplary embodiments, and claims.

BRIEF DESCRIPTION OF THE DRAWINGS

FIG. 2 (SEQ ID NOS: 31-38) depicts GRONs comprising RNA/DNA, referred to herein as "Okazaki Fragment GRONs."

FIG. 3 depicts the native complex and the chimera from LeCong et al.

DETAILED DESCRIPTION OF THE INVENTION

Figure 1:
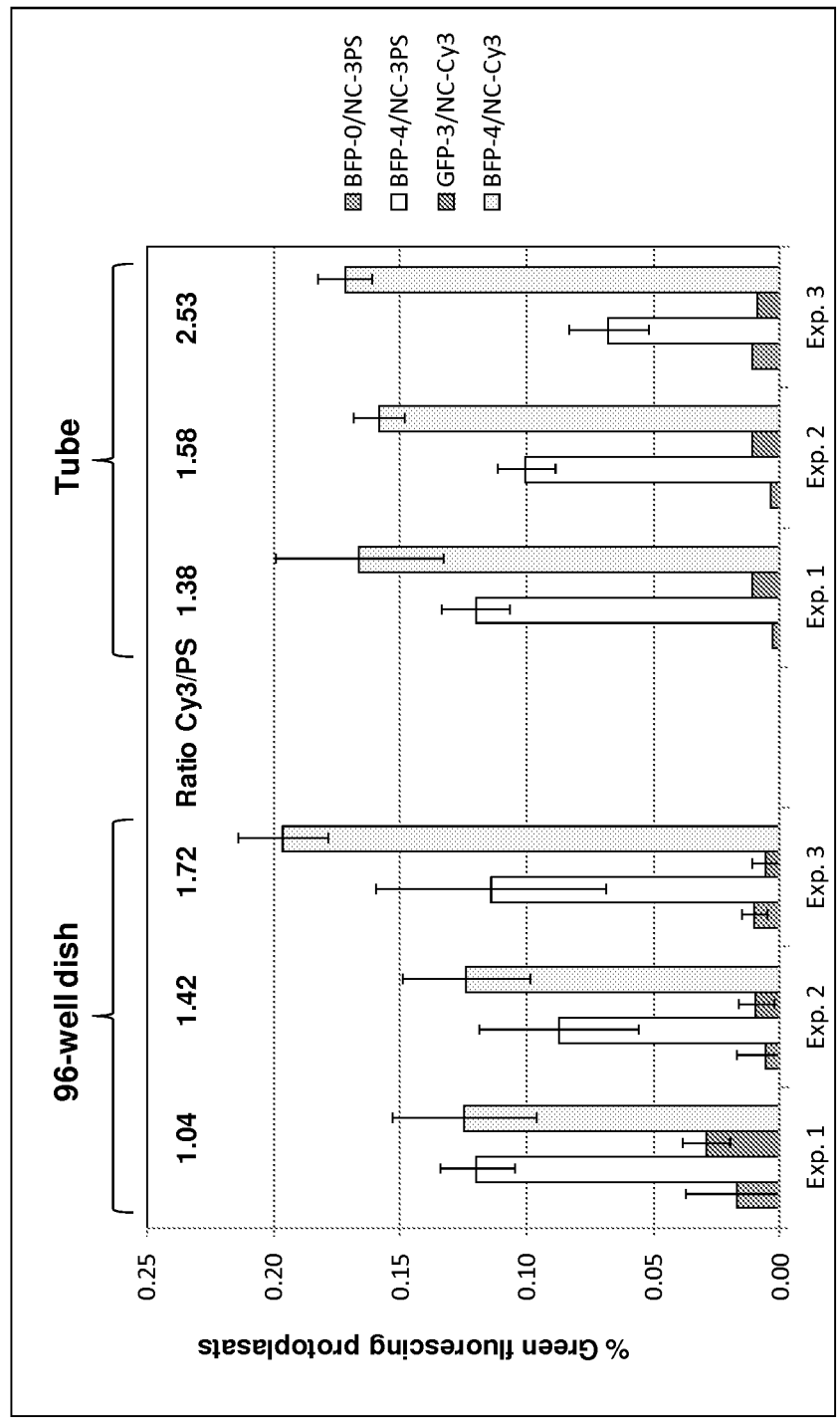
FIG. 1 depicts BFP to GFP conversion mediated by phosphothioate (PS) labeled GRONs (having 3 PS moieties at each end of the GRON) and 5'Cy3/3'idC labeled GRONs.
Figure 4:
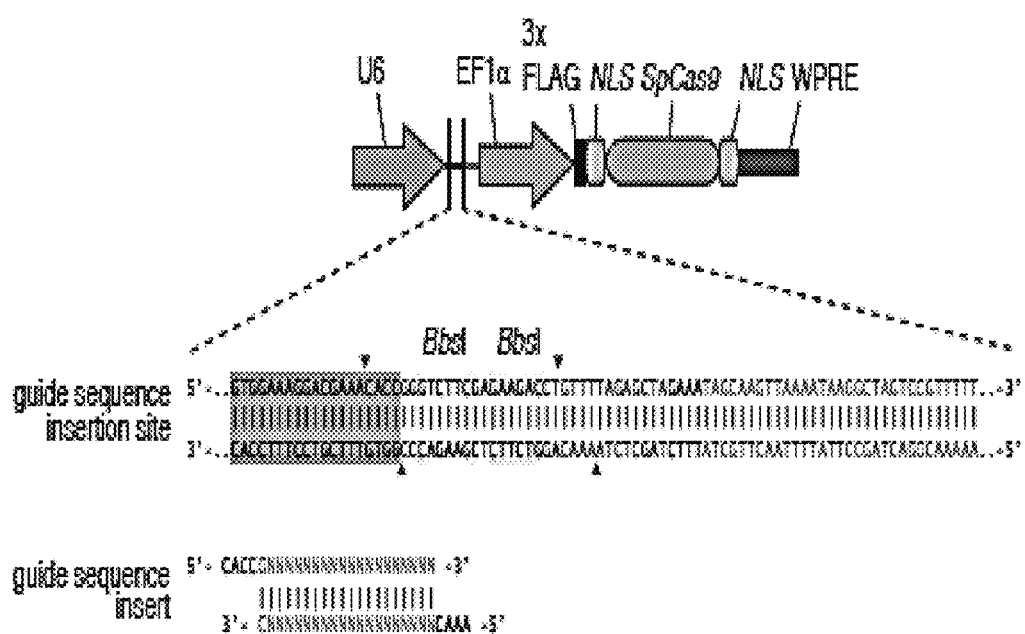
FIG. 4. is a schematic of the expression vector for chimeric crRNA.

Developed over the past few years, targeted genetic modification mediated by oligonucleotides has been shown to be a valuable technique for use in the specific alteration of short stretches of DNA to create deletions, short insertions, and point mutations. These methods involve DNA pairing/annealing, followed by a DNA repair/recombination event. First, the nucleic acid anneals with its complementary strand in the double-stranded DNA in a process mediated by cellular protein factors. This annealing creates a centrally located mismatched base pair (in the case of a point mutation), resulting in a structural perturbation that most likely stimulates the endogenous protein machinery to initiate the second step in the repair process: site-specific modification of the chromosomal sequence and even their organelles (e.g., mitochondria and chloroplasts). This newly introduced mismatch induces the DNA repair machinery to perform a second repair event, leading to the final revision of the target site. The present methods improve these methods by providing novel approaches which increase the availability of DNA repair components, thus increasing the efficiency and reproducibility of gene repair-mediated modifications to targeted nucleic acids.

Definitions

To facilitate understanding of the invention, a number of terms are defined below.

"Nucleic acid sequence," "nucleotide sequence" and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotides" and "oligomers" refer to a nucleic acid sequence of at least about 10 nucleotides and as many as about 201 nucleotides, preferably about 15 to 30 nucleotides, and more preferably about 20-25 nucleotides, which can be used as a probe or amplimer.

The terms "DNA-modifying molecule" and "DNA-modifying reagent" as used herein refer to a molecule which is capable of recognizing and specifically binding to a nucleic acid sequence in the genome of a cell, and which is capable of modifying a target nucleotide sequence within the genome, wherein the recognition and specific binding of the DNA-modifying molecule to the nucleic acid sequence is protein-independent. The term "protein-independent" as used herein in connection with a DNA-modifying molecule means that the DNA-modifying molecule does not require the presence and/or activity of a protein and/or enzyme for the recognition of, and/or specific binding to, a nucleic acid sequence. DNA-modifying molecules are exemplified, but not limited to triplex forming oligonucleotides, peptide nucleic acids, polyamides, and oligonucleotides which are intended to promote gene conversion. The DNA-modifying molecules of the invention are distinguished from the prior art's nucleic acid sequences which are used for homologous recombination [Wong & Capecchi, Molec. Cell. Biol. 7:2294-2295, 1987] in that the prior art's nucleic acid sequences which are used for homologous recombination are protein-dependent. The term "protein-dependent" as used herein in connection with a molecule means that the molecule requires the presence and/or activity of a protein and/or enzyme for the recognition of, and/or specific binding of the molecule to, a nucleic acid sequence. Methods for determining whether a DNA-modifying molecule requires the presence and/or activity of a protein and/or enzyme for the recognition of, and/or specific binding to, a nucleic acid sequence are within the skill in the art [see, e.g., Dennis et al. Nucl. Acids Res. 27:4734-4742, 1999]. For example, the DNA-modifying molecule may be incubated in vitro with the nucleic acid sequence in the absence of any proteins and/or enzymes. The detection of specific binding between the DNA-modifying molecule and the nucleic acid sequence demonstrates that the DNA-modifying molecule is protein-independent. On the other hand, the absence of specific binding between the DNA-modifying molecule and the nucleic acid sequence demonstrates that the DNA-modifying molecule is protein-dependent and/or requires additional factors.

"Triplex forming oligonucleotide" (TFO) is defined as a sequence of DNA or RNA that is capable of binding in the major grove of a duplex DNA or RNA helix to form a triple helix. Although the TFO is not limited to any particular length, a preferred length of the TFO is 200 nucleotides or less, more preferably 100 nucleotides or less, yet more preferably from 5 to 50 nucleotides, even more preferably from 10 to 25 nucleotides, and most preferably from 15 to 25 nucleotides. Although a degree of sequence specificity between the TFO and the duplex DNA is necessary for formation of the triple helix, no particular degree of specificity is required, as long as the triple helix is capable of forming. Likewise, no specific degree of avidity or affinity between the TFO and the duplex helix is required as long as the triple helix is capable of forming. While not intending to limit the length of the nucleotide sequence to which the TFO specifically binds in one embodiment, the nucleotide sequence to which the TFO specifically binds is from 1 to 100, more preferably from 5 to 50, yet more preferably from 10 to 25, and most preferably from 15 to 25, nucleotides. Additionally, "triple helix" is defined as a double-helical nucleic acid with an oligonucleotide bound to a target sequence within the double-helical nucleic acid. The "double-helical" nucleic acid can be any double-stranded nucleic acid including double-stranded DNA, double-stranded RNA and mixed duplexes of DNA and RNA. The double-stranded nucleic acid is not limited to any particular length. However, in preferred embodiments it has a length of greater than 500 bp, more preferably greater than 1 kb and most preferably greater than about 5 kb. In many applications the double-helical nucleic acid is cellular, genomic nucleic acid. The triplex forming oligonucleotide may bind to the target sequence in a parallel or anti-parallel manner.

"Peptide Nucleic Acids," "polyamides" or "PNA" are nucleic acids wherein the phosphate backbone is replaced with an N-aminoethylglycine-based polyamide structure. PNAs have a higher affinity for complementary nucleic acids than their natural counter parts following the Watson-Crick base-pairing rules. PNAs can form highly stable triple helix structures with DNA of the following stoichiometry: (PNA)2.DNA. Although the peptide nucleic acids and polyamides are not limited to any particular length, a preferred length of the peptide nucleic acids and polyamides is 200 nucleotides or less, more preferably 100 nucleotides or less, and most preferably from 5 to 50 nucleotides long. While not intending to limit the length of the nucleotide sequence to which the peptide nucleic acid and polyamide specifically binds, in one embodiment, the nucleotide sequence to which the peptide nucleic acid and polyamide specifically bind is from 1 to 100, more preferably from 5 to 50, yet more preferably from 5 to 25, and most preferably from 5 to 20, nucleotides.

The term "cell" refers to a single cell. The term "cells" refers to a population of cells. The population may be a pure population comprising one cell type. Likewise, the population may comprise more than one cell type. In the present invention, there is no limit on the number of cell types that a cell population may comprise.

The term "synchronize" or "synchronized," when referring to a sample of cells, or "synchronized cells" or "synchronized cell population" refers to a plurality of cells which have been treated to cause the population of cells to be in the same phase of the cell cycle. It is not necessary that all of the cells in the sample be synchronized. A small percentage of cells may not be synchronized with the majority of the cells in the sample. A preferred range of cells that are synchronized is between 10-100%. A more preferred range is between 30-100%. Also, it is not necessary that the cells be a pure population of a single cell type. More than one cell type may be contained in the sample. In this regard, only one of cell types may be synchronized or may be in a different phase of the cell cycle as compared to another cell type in the sample.

The term "synchronized cell" when made in reference to a single cell means that the cell has been manipulated such that it is at a cell cycle phase which is different from the cell cycle phase of the cell prior to the manipulation. Alternatively, a "synchronized cell" refers to a cell that has been manipulated to alter (i.e., increase or decrease) the duration of the cell cycle phase at which the cell was prior to the manipulation when compared to a control cell (e.g., a cell in the absence of the manipulation).

The term "cell cycle" refers to the physiological and morphological progression of changes that cells undergo when dividing (i.e. proliferating). The cell cycle is generally recognized to be composed of phases termed "interphase," "prophase," "metaphase," "anaphase," and "telophase". Additionally, parts of the cell cycle may be termed "M (mitosis)," "S (synthesis)," "G0," "G1 (gap 1)" and "G2 (gap2)". Furthermore, the cell cycle includes periods of progression that are intermediate to the above named phases.

The term "cell cycle inhibition" refers to the cessation of cell cycle progression in a cell or population of cells. Cell cycle inhibition is usually induced by exposure of the cells to an agent (chemical, proteinaceous or otherwise) that interferes with aspects of cell physiology to prevent continuation of the cell cycle.

"Proliferation" or "cell growth" refers to the ability of a parent cell to divide into two daughter cells repeatably thereby resulting in a total increase of cells in the population. The cell population may be in an organism or in a culture apparatus.

The term "capable of modifying DNA" or "DNA modifying means" refers to procedures, as well as endogenous or exogenous agents or reagents that have the ability to induce, or can aid in the induction of, changes to the nucleotide sequence of a targeted segment of DNA. Such changes may be made by the deletion, addition or substitution of one or more bases on the targeted DNA segment. It is not necessary that the DNA sequence changes confer functional changes to any gene encoded by the targeted sequence. Furthermore, it is not necessary that changes to the DNA be made to any particular portion or percentage of the cells.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences that do not encode an mRNA or protein product (e.g., promoter sequence, enhancer sequence, polyadenylation sequence, termination sequence, regulatory RNAs such as miRNA, etc.).

"Amino acid sequence," "polypeptide sequence," "peptide sequence" and "peptide" are used interchangeably herein to refer to a sequence of amino acids.

"Target sequence," as used herein, refers to a double-helical nucleic acid comprising a sequence preferably greater than 8 nucleotides in length but less than 201 nucleotides in length. In some embodiments, the target sequence is preferably between 8 to 30 bases. The target sequence, in general, is defined by the nucleotide sequence on one of the strands on the double-helical nucleic acid.

As used herein, a "purine-rich sequence" or "polypurine sequence" when made in reference to a nucleotide sequence on one of the strands of a double-helical nucleic acid sequence is defined as a contiguous sequence of nucleotides wherein greater than 50% of the nucleotides of the target sequence contain a purine base. However, it is preferred that the purine-rich target sequence contain greater than 60% purine nucleotides, more preferably greater than 75% purine nucleotides, next most preferably greater than 90% purine nucleotides and most preferably 100% purine nucleotides.

As used herein, a "pyrimidine-rich sequence" or "polypyrimidine sequence" when made in reference to a nucleotide sequence on one of the strands of a double-helical nucleic acid sequence is defined as a contiguous sequence of nucleotides wherein greater that 50% of the nucleotides of the target sequence contain a pyrimidine base. However, it is preferred that the pyrimidine-rich target sequence contain greater than 60% pyrimidine nucleotides and more preferably greater than 75% pyrimidine nucleotides. In some embodiments, the sequence contains preferably greater than 90% pyrimidine nucleotides and, in other embodiments, is most preferably 100% pyrimidine nucleotides.

A "variant" of a first nucleotide sequence is defined as a nucleotide sequence which differs from the first nucleotide sequence (e.g., by having one or more deletions, insertions, or substitutions that may be detected using hybridization assays or using DNA sequencing). Included within this definition is the detection of alterations or modifications to the genomic sequence of the first nucleotide sequence. For example, hybridization assays may be used to detect (1) alterations in the pattern of restriction enzyme fragments capable of hybridizing to the first nucleotide sequence when comprised in a genome (i.e., RFLP analysis), (2) the inability of a selected portion of the first nucleotide sequence to hybridize to a sample of genomic DNA which contains the first nucleotide sequence (e.g., using allele-specific oligonucleotide probes), (3) improper or unexpected hybridization, such as hybridization to a locus other than the normal chromosomal locus for the first nucleotide sequence (e.g., using fluorescent in situ hybridization (FISH) to metaphase chromosomes spreads, etc.). One example of a variant is a mutated wild type sequence.

The terms "nucleic acid" and "unmodified nucleic acid" as used herein refer to any one of the known four deoxyribonucleic acid bases (i.e., guanine, adenine, cytosine, and thymine). The term "modified nucleic acid" refers to a nucleic acid whose structure is altered relative to the structure of the unmodified nucleic acid. Illustrative of such modifications would be replacement covalent modifications of the bases, such as alkylation of amino and ring nitrogens as well as saturation of double bonds.

As used herein, the terms "mutation" and "modification" and grammatical equivalents thereof when used in reference to a nucleic acid sequence are used interchangeably to refer to a deletion, insertion, substitution, strand break, and/or introduction of an adduct. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Pyrimidine to pyrimidine (e.g. C to T or T to C nucleotide substitutions) or purine to purine (e.g. G to A or A to G nucleotide substitutions) are termed transitions, whereas pyrimidine to purine or purine to pyrimidine (e.g. G to T or G to C or A to T or A to C) are termed transversions. Alternatively, a nucleic acid may be replaced by a modified nucleic acid as exemplified by replacement of a thymine by thymine glycol. Mutations may result in a mismatch. The term "mismatch" refers to a non-covalent interaction between two nucleic acids, each nucleic acid residing on a different polynucleic acid sequence, which does not follow the base-pairing rules. For example, for the partially complementary sequences 5'-AGT-3' and 5'-AAT-3', a G-A mismatch (a transition) is present. The terms "introduction of an adduct" or "adduct formation" refer to the covalent or non-covalent linkage of a molecule to one or more nucleotides in a DNA sequence such that the linkage results in a reduction (preferably from 10% to 100%, more preferably from 50% to 100%, and most preferably from 75% to 100%) in the level of DNA replication and/or transcription.

The term "strand break" when made in reference to a double stranded nucleic acid sequence includes a single-strand break and/or a double-strand break. A single-strand break (a nick) refers to an interruption in one of the two strands of the double stranded nucleic acid sequence. This is in contrast to a double-strand break which refers to an interruption in both strands of the double stranded nucleic acid sequence. Strand breaks may be introduced into a double stranded nucleic acid sequence either directly (e.g., by ionizing radiation or treatment with certain chemicals) or indirectly (e.g., by enzymatic incision at a nucleic acid base).

The terms "mutant cell" and "modified cell" refer to a cell which contains at least one modification in the cell's genomic sequence.

The term "portion" when used in reference to a nucleotide sequence refers to fragments of that nucleotide sequence. The fragments may range in size from 5 nucleotide residues to the entire nucleotide sequence minus one nucleic acid residue.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

The terms "in operable combination," "in operable order" and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofectin, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total". "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids. For the sake of convenience, the terms "polynucleotides" and "oligonucleotides" include molecules which include nucleosides.

The terms "homology" and "homologous" as used herein in reference to nucleotide sequences refer to a degree of complementarity with other nucleotide sequences. There may be partial homology or complete homology (i.e., identity). When used in reference to a double-stranded nucleic acid sequence such as a cDNA or genomic clone, the term "substantially homologous" refers to any nucleic acid sequence (e.g., probe) which can hybridize to either or both strands of the double-stranded nucleic acid sequence under conditions of low stringency as described above. A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 68° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5×Denhardt's reagent (50×Denhardt's contains per 500 ml:5 g Ficoll (Type 400, Pharmacia), 5 g BSA (Fraction V; Sigma)) and 100 µg/ml denatured salmon sperm DNA followed by washing in a solution comprising 2.0×SSPE, 0.1% SDS at room temperature when a probe of about 100 to about 1000 nucleotides in length is employed.

In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5×Denhardt's reagent and 100 µg/ml denatured salmon sperm DNA followed by washing in a solution comprising 0.1×SSPE and 0.1% SDS at 68° C. when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41(\% \ G+C)$, when a nucleic acid is in aqueous solution at 1 M NaCl (see e.g., Anderson and Young, Quantitative Filter Hybridization, in Nucleic Acid Hybridization, 1985). Other references include more sophisticated computations which take structural as well as sequence characteristics into account for the calculation of Tm.

As used herein the term "stringency" is used in reference to the conditions of temperature, ionic strength, and the presence of other compounds such as organic solvents, under which nucleic acid hybridizations are conducted. "Stringency" typically occurs in a range from about Tm° C. to about 20° C. to 25° C. below Tm. As will be understood by those of skill in the art, a stringent hybridization can be used to identify or detect identical polynucleotide sequences or to identify or detect similar or related polynucleotide sequences.

The terms "specific binding," "binding specificity," and grammatical equivalents thereof when made in reference to the binding of a first nucleotide sequence to a second nucleotide sequence, refer to the preferential interaction between the first nucleotide sequence with the second nucleotide sequence as compared to the interaction between the second nucleotide sequence with a third nucleotide sequence. Specific binding is a relative term that does not require absolute specificity of binding; in other words, the term "specific binding" does not require that the second nucleotide sequence interact with the first nucleotide sequence in the absence of an interaction between the second nucleotide sequence and the third nucleotide sequence. Rather, it is sufficient that the level of interaction between the first nucleotide sequence and the second nucleotide sequence is greater than the level of interaction between the second nucleotide sequence with the third nucleotide sequence. "Specific binding" of a first nucleotide sequence with a second nucleotide sequence also means that the interaction between the first nucleotide sequence and the second nucleotide sequence is dependent upon the presence of a particular structure on or within the first nucleotide sequence; in other words the second nucleotide sequence is recognizing and binding to a specific structure on or within the first nucleotide sequence rather than to nucleic acids or to nucleotide sequences in general. For example, if a second nucleotide sequence is specific for structure "A" that is on or within a first nucleotide sequence, the presence of a third nucleic acid sequence containing structure A will reduce the amount of the second nucleotide sequence which is bound to the first nucleotide sequence.

As used herein, the term "amplifiable nucleic acid" is used in reference to nucleic acids which may be amplified by any amplification method. It is contemplated that "amplifiable nucleic acid" will usually comprise "sample template."

The terms "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Amplification" is defined as the production of additional copies of a nucleic acid sequence and is generally carried out using polymerase chain reaction technologies well known in the art (Dieffenbach C W and G S Dveksler (1995) PCR Primer, a Laboratory Manual, Cold Spring Harbor Press, Plainview, N.Y.). As used herein, the term "polymerase chain reaction" ("PCR") refers to the method of K. B. Mullis U.S. Pat. Nos. 4,683,195, and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

One such preferred method, particularly for commercial applications, is based on the widely used TaqMan® real-time PCR technology, and combines Allele-Specific PCR with a Blocking reagent (ASB-PCR) to suppress amplification of the wildype allele. ASB-PCR can be used for detection of germ line or somatic mutations in either DNA or RNA extracted from any type of tissue, including formalin-fixed paraffin-embedded tumor specimens. A set of reagent design rules are developed enabling sensitive and selective detection of single point substitutions, insertions, or deletions against a background of wild-type allele in thousand-fold or greater excess. (Morlan J, Baker J, Sinicropi D Mutation Detection by Real-Time PCR: A Simple, Robust and Highly Selective Method. PLoS ONE 4(2): e4584, 2009)

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut or nick double- or single-stranded DNA at or near a specific nucleotide sequence, for example, an endonuclease domain of a type IIS restriction endonuclease (e.g., FokI) can be used, as taught by Kim et al., 1996, Proc. Nat'l. Acad. Sci. USA, 6:1 156-60).

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Additionally "an oligonucleotide having a nucleotide sequence encoding a gene" may include suitable control elements such as enhancers, promoters, splice junctions, polyadenylation signals, etc. if needed to permit proper initiation of transcription and/or correct processing of the primary RNA transcript. Further still, the coding region of the present invention may contain endogenous enhancers, splice junctions, intervening sequences, polyadenylation signals, etc.

Transcriptional control signals in eukaryotes comprise "enhancer" elements. Enhancers consist of short arrays of DNA sequences that interact specifically with cellular proteins involved in transcription (Maniatis, T. et al., Science 236:1237, 1987). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook, J. et al., Molecular Cloning: A Laboratory Manual, 2nd ed., Cold Spring Harbor Laboratory Press, New York, pp. 16.7-16.8, 1989). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "promoter," "promoter element" or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

The term "tissue specific" as it applies to a promoter refers to a promoter that is capable of directing selective expression of an oligonucleotide sequence to a specific type of tissue in the relative absence of expression of the same oligonucleotide in a different type of tissue. Tissue specificity of a promoter may be evaluated by, for example, operably linking a reporter gene to the promoter sequence to generate a reporter construct, introducing the reporter construct into the genome of a plant or an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic plant or animal. Selectivity need not be absolute. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter which is capable of directing selective expression of an oligonucleotide sequence in a specific type of cell in the relative absence of expression of the same oligonucleotide sequence in a different type of cell within the same tissue. The term "cell type specific" when applied to a promoter also means a promoter capable of promoting selective expression of an oligonucleotide in a region within a single tissue. Again, selectivity need not be absolute. Cell type specificity of a promoter may be assessed using methods well known in the art, e.g., immunohistochemical staining as described herein. Briefly, tissue sections are embedded in paraffin, and paraffin sections are reacted with a primary antibody which is specific for the polypeptide product encoded by the oligonucleotide sequence whose expression is controlled by the promoter. As an alternative to paraffin sectioning, samples may be cryosectioned. For example, sections may be frozen prior to and during sectioning thus avoiding potential interference by residual paraffin. A labeled (e.g., peroxidase conjugated) secondary antibody which is specific for the primary antibody is allowed to bind to the sectioned tissue and specific binding detected (e.g., with avidin/biotin) by microscopy.

The terms "selective expression," "selectively express" and grammatical equivalents thereof refer to a comparison of relative levels of expression in two or more regions of interest. For example, "selective expression" when used in connection with tissues refers to a substantially greater level of expression of a gene of interest in a particular tissue, or to a substantially greater number of cells which express the gene within that tissue, as compared, respectively, to the level of expression of, and the number of cells expressing, the same gene in another tissue (i.e., selectivity need not be absolute). Selective expression does not require, although it may include, expression of a gene of interest in a particular tissue and a total absence of expression of the same gene in another tissue. Similarly, "selective expression" as used herein in reference to cell types refers to a substantially greater level of expression of, or a substantially greater number of cells which express, a gene of interest in a particular cell type, when compared, respectively, to the expression levels of the gene and to the number of cells expressing the gene in another cell type.

The term "contiguous" when used in reference to two or more nucleotide sequences means the nucleotide sequences are ligated in tandem either in the absence of intervening sequences, or in the presence of intervening sequences which do not comprise one or more control elements.

As used herein, the terms "nucleic acid molecule encoding," "nucleotide encoding," "DNA sequence encoding" and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the term "purified" or "to purify" refers to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "substantially purified" refers to molecules, either nucleic or amino acid sequences, that are removed from their natural environment, isolated or separated, and are at least 60% free, preferably 75% free and more preferably 90% free from other components with which they are naturally associated. An "isolated polynucleotide" is, therefore, a substantially purified polynucleotide.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side generally by the nucleotide triplet "ATG" which encodes the initiator methionine and on the 3' side by one of the three triplets which specify stop codons (i.e., TAA, TAG, TGA).

By "coding sequence" is meant a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

By "non-coding sequence" is meant a sequence of a nucleic acid or its complement, or a part thereof that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "peptide transcription factor binding site" or "transcription factor binding site" refers to a nucleotide sequence which binds protein transcription factors and, thereby, controls some aspect of the expression of nucleic acid sequences. For example, Sp-1 and AP1 (activator protein 1) binding sites are examples of peptide transcription factor binding sites.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia. "Non-human animal" additionally refers to amphibians (e.g. *Xenopus*), reptiles, insects (e.g. *Drosophila*) and other non-mammalian animal species.

As used herein, the term "transgenic" refers to an organism or cell that has DNA derived from another organism inserted into which becomes integrated into the genome either of somatic and/or germ line cells of the plant or animal. A "transgene" means a DNA sequence which is partly or entirely heterologous (i.e., not present in nature) to the plant or animal in which it is found, or which is homologous to an endogenous sequence (i.e., a sequence that is found in the animal in nature) and is inserted into the plant' or animal's genome at a location which differs from that of the naturally occurring sequence. Transgenic plants or animals which include one or more transgenes are within the scope of this invention. Additionally, a "transgenic" as used herein refers to an animal that has had one or more genes modified and/or "knocked out" (made non-functional or made to function at reduced level, i.e., a "knockout" mutation) by the invention's methods, by homologous recombination, TFO mutation or by similar processes. For example, in some embodiments, a transgenic organism or cell includes inserted DNA that includes a foreign promoter and/or coding region.

A "transformed cell" is a cell or cell line that has acquired the ability to grow in cell culture for multiple generations, the ability to grow in soft agar, and/or the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, nucleofection and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

As used herein "exogenous" means that the gene encoding the protein is not normally expressed in the cell. Additionally, "exogenous" refers to a gene transfected into a cell to augment the normal (i.e. natural) level of expression of that gene.

A peptide sequence and nucleotide sequence may be "endogenous" or "heterologous" (i.e., "foreign"). The term "endogenous" refers to a sequence which is naturally found in the cell into which it is introduced so long as it does not contain some modification relative to the naturally-occurring sequence. The term "heterologous" refers to a sequence which is not endogenous to the cell into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence. Generally, although not necessarily, heterologous DNA encodes heterologous RNA and heterologous proteins that are not normally produced by the cell into which it is introduced. Examples of heterologous DNA include reporter genes, transcriptional and translational regulatory sequences, DNA sequences which encode selectable marker proteins (e.g., proteins which confer drug resistance), etc.

Constructs

The nucleic acid molecules disclosed herein (e.g., site specific nucleases, or guide RNA for CRISPRs) can be used in the production of recombinant nucleic acid constructs. In one embodiment, the nucleic acid molecules of the present disclosure can be used in the preparation of nucleic acid constructs, for example, expression cassettes for expression in the plant of interest. This expression may be transient for instance when the construct is not integrated into the host genome or maintained under the control offered by the promoter and the position of the construct within the host's genome if it becomes integrated.

Expression cassettes may include regulatory sequences operably linked to the site specific nuclease or guide RNA sequences disclosed herein. The cassette may additionally contain at least one additional gene to be co-transformed into the organism. Alternatively, the additional gene(s) can be provided on multiple expression cassettes.

The nucleic acid constructs may be provided with a plurality of restriction sites for insertion of the site specific nuclease coding sequence to be under the transcriptional regulation of the regulatory regions. The nucleic acid constructs may additionally contain nucleic acid molecules encoding for selectable marker genes.

Any promoter can be used in the production of the nucleic acid constructs. The promoter may be native or analogous, or foreign or heterologous, to the plant host nucleic acid sequences disclosed herein. Additionally, the promoter may be the natural sequence or alternatively a synthetic sequence. Where the promoter is "foreign" or "heterologous" to the plant host, it is intended that the promoter is not found in the native plant into which the promoter is introduced. As used herein, a chimeric gene comprises a coding sequence operably linked to a transcription initiation region that is heterologous to the coding sequence.

The site directed nuclease sequences disclosed herein may be expressed using heterologous promoters.

Any promoter can be used in the preparation of constructs to control the expression of the site directed nuclease sequences, such as promoters providing for constitutive, tissue-preferred, inducible, or other promoters for expression in plants. Constitutive promoters include, for example, the core promoter of the Rsyn7 promoter and other constitutive promoters disclosed in WO 99/43 838 and U.S. Pat. No. 6,072,050; the core CaMV 35S promoter (Odell et al. Nature 313:810-812; 1985); rice actin (McElroy et al., Plant Cell 2:163-171, 1990); ubiquitin (Christensen et al., Plant Mol. Biol. 12:619-632, 1989 and Christensen et al., Plant Mol. Biol. 18:675-689, 1992); pEMU (Last et al., Theor. Appl. Genet. 81:581-588, 1991); MAS (Velten et al., EMBO J. 3:2723-2730, 1984); ALS promoter (U.S. Pat. No. 5,659, 026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to direct site directed nuclease expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al., Plant J. 12(2): 255-265, 1997; Kawamata et al., Plant Cell Physiol. 38(7): 792-803, 1997; Hansen et al., Mol. Gen Genet. 254(3):337-343, 1997; Russell et al., Transgenic Res. 6(2):157-168, 1997; Rinehart et al., Plant Physiol. 1 12(3):1331-1341, 1996; Van Camp et al., Plant Physiol. 1 12(2):525-535, 1996; Canevascini et al., Plant Physiol. 112(2): 513-524, 1996; Yamamoto et al., Plant Cell Physiol. 35(5):773-778, 1994; Lam, Results Probl. Cell Differ. 20:181-196, 1994; Orozco et al. Plant Mol Biol. 23(6): 1129-1138, 1993; Matsuoka et al., Proc Nat'l. Acad. Sci. USA 90(20):9586-9590, 1993; and Guevara-Garcia et al., Plant J. 4(3):495-505, 1993.

The nucleic acid constructs may also include transcription termination regions. Where transcription terminations regions are used, any termination region may be used in the preparation of the nucleic acid constructs. For example, the termination region may be derived from another source (i.e., foreign or heterologous to the promoter). Examples of termination regions that are available for use in the constructs of the present disclosure include those from the Ti-plasmid of *A. tumefaciens*, such as the octopine synthase and nopaline synthase termination regions. See also Guerineau et al., Mol. Gen. Genet. 262:141-144, 1991; Proudfoot, Cell 64:671-674, 1991; Sanfacon et al., Genes Dev. 5:141-149, 1991; Mogen et al., Plant Cell 2:1261-1272, 1990; Munroe et al., Gene 91:151-158, 1990; Ballas et al., Nucleic Acids Res. 17:7891-7903, 1989; and Joshi et al., Nucleic Acid Res. 15:9627-9639, 1987.

In conjunction with any of the aspects, embodiments, methods and/or compositions disclosed herein, the nucleic acids may be optimized for increased expression in the transformed plant. That is, the nucleic acids encoding the site directed nuclease proteins can be synthesized using plant-preferred codons for improved expression. See, for example, Campbell and Gowri, (Plant Physiol. 92:1-11, 1990) for a discussion of host-preferred codon usage. Methods are available in the art for synthesizing plant-preferred genes. See, for example, U.S. Pat. Nos. 5,380,831, and 5,436,391, and Murray et al., Nucleic Acids Res. 17:477-498, 1989.

In addition, other sequence modifications can be made to the nucleic acid sequences disclosed herein. For example, additional sequence modifications are known to enhance gene expression in a cellular host. These include elimination of sequences encoding spurious polyadenylation signals, exon/intron splice site signals, transposon-like repeats, and other such well-characterized sequences that may be deleterious to gene expression. The G-C content of the sequence may also be adjusted to levels average for a target cellular host, as calculated by reference to known genes expressed in the host cell. In addition, the sequence can be modified to avoid predicted hairpin secondary mRNA structures.

Other nucleic acid sequences may also be used in the preparation of the constructs of the present disclosure, for example to enhance the expression of the site directed nuclease coding sequence. Such nucleic acid sequences include the introns of the maize AdhI, intron1 gene (Callis et al., Genes and Development 1:1183-1200, 1987), and leader sequences, (W-sequence) from the Tobacco Mosaic virus (TMV), Maize Chlorotic Mottle Virus and Alfalfa Mosaic Virus (Gallie et al., Nucleic Acid Res. 15:8693-8711, 1987; and Skuzeski et al., Plant Mol. Biol. 15:65-79, 1990). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize site directed nuclease gene expression, the plant expression vectors disclosed herein may also contain DNA sequences containing matrix attachment regions (MARs). Plant cells transformed with such modified expression systems, then, may exhibit overexpression or constitutive expression of a nucleotide sequence of the disclosure.

The expression constructs disclosed herein can also include nucleic acid sequences capable of directing the expression of the site directed nuclease sequence to the chloroplast. Such nucleic acid sequences include chloroplast targeting sequences that encodes a chloroplast transit peptide to direct the gene product of interest to plant cell chloroplasts. Such transit peptides are known in the art. With respect to chloroplast-targeting sequences, "operably linked" means that the nucleic acid sequence encoding a transit peptide (i.e., the chloroplast-targeting sequence) is linked to the site directed nuclease nucleic acid molecules disclosed herein such that the two sequences are contiguous and in the same reading frame. See, for example, Von Heijne et al., Plant Mol. Biol. Rep. 9:104-126, 1991; Clark et al., J. Biol. Chem. 264:17544-17550, 1989; Della-Cioppa et al., Plant Physiol. 84:965-968, 1987; Romer et al., Biochem. Biophys. Res. Commun. 196:1414-1421, 1993; and Shah et al., Science 233:478-481, 1986.

Chloroplast targeting sequences are known in the art and include the chloroplast small subunit of ribulose-1,5-bisphosphate carboxylase (Rubisco) (de Castro Silva Filho et al., Plant Mol. Biol. 30:769-780, 1996; Schnell et al., J. Biol. Chem. 266(5):3335-3342, 1991); 5-(enolpyruvyl)shikimate-3-phosphate synthase (EPSPS) (Archer et al., J. Bioenerg. Biomemb. 22(6):789-810, 1990); tryptophan synthase (Zhao et al., J. Biol. Chem. 270(1 1):6081-6087, 1995); plastocyanin (Lawrence et al., J. Biol. Chem. 272(33):20357-20363, 1997); chorismate synthase (Schmidt et al., J. Biol. Chem. 268(36):27447-27457, 1993); and the light harvesting chlorophyll a/b binding protein (LHBP) (Lamppa et al., J. Biol. Chem. 263:14996-14999, 1988). See also Von Heijne et al., Plant Mol. Biol. Rep. 9:104-126, 1991; Clark et al., J. Biol. Chem. 264:17544-17550, 1989; Della-Cioppa et al., Plant Physiol. 84:965-968, 1987; Romer et al., Biochem. Biophys. Res. Commun. 196:1414-1421, 1993; and Shah et al., Science 233:478-481, 1986.

In conjunction with any of the aspects, embodiments, methods and/or compositions disclosed herein, the nucleic acid constructs may be prepared to direct the expression of the mutant site directed nuclease coding sequence from the plant cell chloroplast. Methods for transformation of chloroplasts are known in the art. See, for example, Svab et al., Proc. Nat'l. Acad. Sci. USA 87:8526-8530, 1990; Svab and Maliga, Proc. Nat'l. Acad. Sci. USA 90:913-917, 1993; Svab and Maliga, EMBO J. 12:601-606, 1993. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. Proc. Nat'l. Acad. Sci. USA 91:7301-7305, 1994.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The nucleic acid constructs can be used to transform plant cells and regenerate transgenic plants comprising the site directed nuclease coding sequences. Numerous plant transformation vectors and methods for transforming plants are available. See, for example, U.S. Pat. No. 6,753,458, An, G. et al., Plant Physiol., 81:301-305, 1986; Fry, J. et al., Plant Cell Rep. 6:321-325, 1987; Block, M., Theor. Appl Genet. 76:767-774, 1988; Hinchee et al., Stadler. Genet. Symp. 203212.203-212, 1990; Cousins et al., Aust. J. Plant Physiol. 18:481-494, 1991; Chee, P. P. and Slightom, J. L., Gene. 118:255-260, 1992; Christou et al., Trends. Biotechnol. 10:239-246, 1992; D'Halluin et al., Bio/Technol. 10:309-3 14, 1992; Dhir et al., Plant Physiol. 99:81-88, 1992; Casas et al., Proc. Nat'l. Acad Sci. USA 90:11212-11216, 1993; Christou, P., In Vitro Cell. Dev. Biol.-Plant 29P: 1 19-124, 1993; Davies, et al., Plant Cell Rep. 12:180-183, 1993; Dong, J. A. and Mc Hughen, A., Plant Sci. 91:139-148, 1993; Franklin, C. I. and Trieu, T. N., Plant. Physiol. 102:167, 1993; Golovkin et al., Plant Sci. 90:41-52, 1993; Guo Chin Sci. Bull. 38:2072-2078; Asano, et al., Plant Cell Rep. 13, 1994; Ayeres N. M. and Park, W. D., Crit. Rev. Plant. Sci. 13:219-239, 1994; Barcelo et al., Plant. J. 5:583-592, 1994; Becker, et al., Plant. J. 5:299-307, 1994; Borkowska et al., Acta. Physiol Plant. 16:225-230, 1994; Christou, P., Agro. Food. Ind. Hi Tech. 5:17-27, 1994; Eapen et al., Plant Cell Rep. 13:582-586, 1994; Hartman et al., Bio-Technology 12:919923, 1994; Ritala et al., Plant. Mol. Biol. 24:317-325, 1994; and Wan, Y. C. and Lemaux, P. G., Plant Physiol. 104:3748, 1994. The constructs may also be transformed into plant cells using homologous recombination.

The term "wild-type" when made in reference to a peptide sequence and nucleotide sequence refers to a peptide sequence and nucleotide sequence (locus/gene/allele), respectively, which has the characteristics of that peptide sequence and nucleotide sequence when isolated from a naturally occurring source. A wild-type peptide sequence and nucleotide sequence is that which is most frequently observed in a population and is thus arbitrarily designated the "normal" or "wild-type" form of the peptide sequence and nucleotide sequence, respectively. "Wild-type" may also refer to the sequence at a specific nucleotide position or positions, or the sequence at a particular codon position or positions, or the sequence at a particular amino acid position or positions.

"Consensus sequence" is defined as a sequence of amino acids or nucleotides that contain identical amino acids or nucleotides or functionally equivalent amino acids or nucleotides for at least 25% of the sequence. The identical or functionally equivalent amino acids or nucleotides need not be contiguous.

The term "*Brassica*" as used herein refers to plants of the *Brassica* genus. Exemplary *Brassica* species include, but are not limited to, *B. carinata, B. elongate, B. fruticulosa, B. juncea, B. napus, B. narinosa, B. nigra, B. oleracea, B. perviridis, B. rapa* (syn *B. campestris*), *B. rupestris, B. septiceps*, and *B. tournefortii*.

A nucleobase is a base, which in certain preferred embodiments is a purine, pyrimidine, or a derivative or analog thereof. Nucleosides are nucleobases that contain a pentosefuranosyl moiety, e.g., an optionally substituted riboside or 2'-deoxyriboside. Nucleosides can be linked by one of several linkage moieties, which may or may not contain phosphorus. Nucleosides that are linked by unsubstituted phosphodiester linkages are termed nucleotides. The term "nucleobase" as used herein includes peptide nucleobases, the subunits of peptide nucleic acids, and morpholine nucleobases as well as nucleosides and nucleotides.

An oligonucleobase is a polymer comprising nucleobases; preferably at least a portion of which can hybridize by Watson-Crick base pairing to a DNA having the complementary sequence. An oligonucleobase chain may have a single 5' and 3' terminus, which are the ultimate nucleobases of the polymer. A particular oligonucleobase chain can contain nucleobases of all types. An oligonucleobase compound is a compound comprising one or more oligonucleobase chains that may be complementary and hybridized by Watson-Crick base pairing. Ribo-type nucleobases include pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

In certain embodiments, an oligonucleobase strand may include both oligonucleobase chains and segments or regions of oligonucleobase chains. An oligonucleobase strand may have a 3' end and a 5' end, and when an oligonucleobase strand is coextensive with a chain, the 3' and 5' ends of the strand are also 3' and 5' termini of the chain.

The term "gene repair oligonucleobase" as used herein denotes oligonucleobases, including mixed duplex oligonucleotides, non-nucleotide containing molecules, single stranded oligodeoxynucleotides and other gene repair molecules.

As used herein the term "codon" refers to a sequence of three adjacent nucleotides (either RNA or DNA) constituting the genetic code that determines the insertion of a specific amino acid in a polypeptide chain during protein synthesis or the signal to stop protein synthesis. The term "codon" is also used to refer to the corresponding (and complementary) sequences of three nucleotides in the messenger RNA into which the original DNA is transcribed.

As used herein, the term "homology" refers to sequence similarity among proteins and DNA. The term "homology" or "homologous" refers to a degree of identity. There may be partial homology or complete homology. A partially homologous sequence is one that has less than 100% sequence identity when compared to another sequence.

"Heterozygous" refers to having different alleles at one or more genetic loci in homologous chromosome segments. As used herein "heterozygous" may also refer to a sample, a cell, a cell population or an organism in which different alleles at one or more genetic loci may be detected. Heterozygous samples may also be determined via methods known in the art such as, for example, nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In other embodiments, the smaller peak is at least about 10% of the larger peak. In other embodiments, the smaller peak is at least about 5% of the larger peak. In other embodiments, a minimal amount of the smaller peak is detected.

As used herein, "homozygous" refers to having identical alleles at one or more genetic loci in homologous chromosome segments. "Homozygous" may also refer to a sample, a cell, a cell population or an organism in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

The term "hemizygous" refers to a gene or gene segment being present only once in the genotype of a cell or an organism because the second allele is deleted. As used herein "hemizygous" may also refer to a sample, a cell, a cell population or an organism in which an allele at one or more genetic loci may be detected only once in the genotype.

The term "zygosity status" as used herein refers to a sample, a cell population, or an organism as appearing heterozygous, homozygous, or hemizygous as determined by testing methods known in the art and described herein.

The term "zygosity status of a nucleic acid" means determining whether the source of nucleic acid appears heterozygous, homozygous, or hemizygous. The "zygosity status" may refer to differences in a single nucleotide in a sequence. In some methods, the zygosity status of a sample with respect to a single mutation may be categorized as homozygous wild-type, heterozygous (i.e., one wild-type allele and one mutant allele), homozygous mutant, or hemizygous (i.e., a single copy of either the wild-type or mutant allele).

As used herein, the term "RTDS" refers to The Rapid Trait Development System™ (RTDS) developed by Cibus. RTDS is a site-specific gene modification system that is effective at making precise changes in a gene sequence without the incorporation of foreign genes or control sequences.

The term "about" as used herein means in quantitative terms plus or minus 10%. For example, "about 3%" would encompass 2.7-3.3% and "about 10%" would encompass 9-11%.

Repair Oligonucleotides

This invention generally relates to novel methods to improve the efficiency of the targeting of modifications to specific locations in genomic or other nucleotide sequences. Additionally, this invention relates to target DNA that has been modified, mutated or marked by the approaches disclosed herein. The invention also relates to cells, tissue, and organisms which have been modified by the invention's methods. The present invention builds on the development of compositions and methods related in part to the successful conversion system, the Rapid Trait Development System (RTDS™, Cibus US LLC).

RTDS is based on altering a targeted gene by utilizing the cell's own gene repair system to specifically modify the gene sequence in situ and not insert foreign DNA and gene expression control sequences. This procedure effects a precise change in the genetic sequence while the rest of the genome is left unaltered. In contrast to conventional transgenic GMOs, there is no integration of foreign genetic material, nor is any foreign genetic material left in the plant. The changes in the genetic sequence introduced by RTDS are not randomly inserted. Since affected genes remain in their native location, no random, uncontrolled or adverse pattern of expression occurs.

The RTDS that effects this change is a chemically synthesized oligonucleotide which may be composed of both DNA and modified RNA bases as well as other chemical moieties, and is designed to hybridize at the targeted gene location to create a mismatched base-pair(s). This mismatched base-pair acts as a signal to attract the cell's own natural gene repair system to that site and correct (replace, insert or delete) the designated nucleotide(s) within the gene. Once the correction process is complete the RTDS molecule is degraded and the now-modified or repaired gene is expressed under that gene's normal endogenous control mechanisms.

The methods and compositions disclosed herein can be practiced or made with "gene repair oligonucleobases" (GRON) having the conformations and chemistries as described in detail below. The "gene repair oligonucleobases" as contemplated herein have also been described in published scientific and patent literature using other names including "recombinagenic oligonucleobases;" "RNA/DNA chimeric oligonucleotides;" "chimeric oligonucleotides;" "mixed duplex oligonucleotides" (MDONs); "RNA DNA oligonucleotides (RDOs);" "gene targeting oligonucleotides;" "genoplasts;" "single stranded modified oligonucleotides;" "Single stranded oligodeoxynucleotide mutational vectors" (SSOMVs); "duplex mutational vectors;" and "heteroduplex mutational vectors." The gene repair oligonucleobase can be introduced into a plant cell using any method commonly used in the art, including but not limited to, microcarriers (biolistic delivery), microfibers, polyethylene glycol (PEG)-mediated uptake, electroporation, and microinjection.

In one embodiment, the gene repair oligonucleobase is a mixed duplex oligonucleotides (MDON) in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a T-OH substituted with a substituent described in the Martin Applications or Sproat is termed a "T-Substituted Ribonucleotide." As used herein the term "RNA-type nucleotide" means a T-hydroxyl or 2'-Substituted Nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a T-H, which can be linked to other nucleotides of a gene repair oligonucleobase by an unsubstituted phosphodiester linkage or any of the non-natural linkages taught by Kmiec I or Kmiec II.

In a particular embodiment of the present invention, the gene repair oligonucleobase is a mixed duplex oligonucleotide (MDON) that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2'-Substituted Ribonucleotides are 2'-fluoro, T-methoxy, 2'-propyloxy, 2'-allyloxy, 2'-hydroxylethyloxy, 2'-methoxyethyloxy, T-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds, Although mixed duplex oligonucleotides (MDONs) having only a single type of 2'-substituted RNA-type nucleotide are more conveniently synthesized, the methods of the invention can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses terms such as "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identical to the length of the heterologous region where a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

In another embodiment of the present invention, the gene repair oligonucleobase (GRON) is a single stranded oligodeoxynucleotide mutational vector (SSOMV), which is disclosed in International Patent Application PCT/USOO/23457, U.S. Pat. Nos. 6,271,360, 6,479,292, and 7,060,500 which is incorporated by reference in its entirety. The sequence of the SSOMV is based on the same principles as the mutational vectors described in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; and WO 99/40789. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. Alternatively, the homologous regions in the SSOMV can be contiguous to each other, while the regions in the target gene having the same sequence are separated by one, two or more nucleotides. Such an SSOMV causes a deletion from the target gene of the nucleotides that are absent from the SSOMV. Lastly, the sequence of the target gene that is identical to the homologous regions may be adjacent in the target gene but separated by one, two, or more nucleotides in the sequence of the SSOMV. Such an SSOMV causes an insertion in the sequence of the target gene.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotide and the targeted nucleotide be a pyrimidine. To the extent that is consistent with achieving the desired functional result, it is preferred that both the mutator nucleotide and the targeted nucleotide in the complementary strand be pyrimidines. Particularly preferred are SSOMVs that encode transversion mutations, i.e., a C or T mutator nucleotide is mismatched, respectively, with a C or T nucleotide in the complementary strand.

Improving Efficiency

The present invention describes a number of approaches to increase the effectiveness of conversion of a target gene using repair oligonucleotides, and which may be used alone or in combination with one another. These include:

1. Introducing modifications to the repair oligonucleotides which attract DNA repair machinery to the targeted (mismatch) site.
    A. Introduction of one or more abasic sites in the oligonucleotide (e.g., within 10 bases, and more preferably with 5 bases of the desired mismatch site) generates a lesion which is an intermediate in base excision repair (BER), and which attracts BER machinery to the vicinity of the site targeted for conversion by the repair oligonucleotide. dSpacer (abasic furan) modified oligonucleotides may be prepared as described in, for example, Takeshita et al., *J. Biol. Chem.*, 262:10171-79, 1987.
    B. Inclusion of compounds which induce single or double strand breaks, either into the oligonucleotide or together with the oligonucleotide, generates a lesion which is repaired by non-homologous end joining (NHEJ), microhomology-mediated end joining (MMEJ), and homologous recombination. By way of example, the bleomycin family of antibiotics, zinc fingers, FokI (or any type IIS class of restriction enzyme) and other nucleases may be covalently coupled to the 3' or 5' end of repair oligonucleotides, in order to introduce double strand breaks in the vicinity of the site targeted for conversion by the repair oligonucleotide. The bleomycin family of antibiotics are DNA cleaving glycopeptides include bleomycin, zeocin, phleomycin, tallysomycin, pepleomycin and others.

C. Introduction of one or more 8'oxo dA or dG incorporated in the oligonucleotide (e.g., within 10 bases, and more preferably with 5 bases of the desired mismatch site) generates a lesion which is similar to lesions created by reactive oxygen species. These lesions induce the so-called "pushing repair" system. See, e.g., Kim et al., J. Biochem. Mol. Biol. 37:657-62, 2004.

2. Increase stability of the repair oligonucleotides:

Introduction of a reverse base (idC) at the 3' end of the oligonucleotide to create a 3' blocked end on the repair oligonucleotide.

Introduction of one or more 2'O-methyl nucleotides or bases which increase hybridization energy (see, e.g., WO2007/073149) at the 5' and/or 3' of the repair oligonucleotide.

Introduction of a plurality of 2'O-methyl RNA nucleotides at the 5' end of the repair oligonucleotide, leading into DNA bases which provide the desired mismatch site, thereby creating an Okazaki Fragment-like nucleic acid structure.

Conjugated (5' or 3') intercalating dyes such as acridine, psoralen, ethidium bromide and Syber stains.

Introduction of a 5' terminus cap such as a T/A clamp, a cholesterol moiety, SIMA (HEX), riboC and amidite.

Backbone modifications such as phosphothioate, 2'-O methyl, methyl phosphonates, locked nucleic acid (LNA), MOE (methoxyethyl), di PS and peptide nucleic acid (PNA).

Crosslinking of the repair oligonucleotide, e.g., with intrastrand crosslinking reagents agents such as cisplatin and mitomycin C.

Conjugation with fluorescent dyes such as Cy3, DY547, Cy3.5, Cy3B, Cy5 and DY647.

3. Increase hybridization energy of the repair oligonucleotide through incorporation of bases which increase hybridization energy (see, e.g., WO2007/073149).

4. Increase the quality of repair oligonucleotide synthesis by using nucleotide multimers (dimers, trimers, tetramers, etc.) as building blocks for synthesis. This results in fewer coupling steps and easier separation of the full length products from building blocks.

5. Use of long repair oligonucleotides (i.e., greater than 55 nucleotides in length, preferably between 75 and 300 nucleotides in length, more preferably at least 100 nucleotides in length, still more preferably at least 150 nucleotides in length, and most preferably at least 200 nucleotides in length), preferably with two or more mutations targeted in the repair oligonucleotide.

Examples of the foregoing approaches are provided in the following table

TABLE 1

GRON chemistries to be tested..

| Oligo type | | Modifications |
|---|---|---|
| 5' mods | T/A clamp | T/A clamp |
| Backbone modifications | Phosphothioate | PS |
| Intercalating dyes | 5' Acridine 3' | idC Acridine, idC |
| Okasaki fragments | | DNA/RNA |
| Cy3 replacements | | DY547 |
| Facilitators | 2'0Me oligos designed 5' and 3' of the converting oligo | 2'0Me |
| Abasic | Abasic site placed in various locations 5' and 3' to the converting base. 44 mer | Abasic 2 |
| Assist | Assist approach Overlap: 2 oligos: 1 with Cy3/idC, 1 unmodified repair oligo | Cy3, idC on one, none on the other: |
| Assist | Assist approach No overlap: 2 oligos: 1 with Cy3/idC, 1 unmodified repair oligo | only make the unmodified oligo |
| Abasic | THF site placed in various locations 5' and 3' to the converting base. 44 mer | Tetrahydrofuran (dspacer) |
| Backbone modifications | 9 | 2'0Me |
| Trimers | | Trimer amidites, Cy3, idC |
| Pushing repair | | 8'oxo dA, 5' Cy3, idC |
| Pushing repair | | 8'oxo dA, 5' Cy3, idC |
| Double Strand break | | Bleomycin |
| Crosslinker | | Cisplatin |
| Crosslinker | | Mitomycin C |
| Facilitators | super bases 5' and 3' of converting oligo | 2 amino dA and 2- thio T |
| Super oligos | | 2'amino d, 5' Cy3, idC |
| Super oligos | | 2-thio T, 5' Cy3, idC |
| Super oligos | | 7-deaza A, 5' Cy3, idC |
| Super oligos | | 7-deaza G, 5' Cy3, idC |
| Super oligos | | propanyl dC, 5' Cy3, idC |
| Intercalating dyes | 5' Psoralen/3' idC | Psoralen, idC |
| Intercalating dyes | 5' Ethidium bromide | |
| Intercalating dyes | 5' Syber stains | |
| 5' mods | 5' Chol/3' idC | Cholesterol |
| Double mutation | Long oligo (100 bases) w/ 2 mutation | Unlmown |
| 5' mods | 5' SIMA HEX/3'idC | SIMA HEX, idC |
| Backbone modifications | 9 | Methyl phosphonates |
| Backbone modifications | | LNA |
| Backbone modifications | 1 | MOE (methoxyethyl) |
| Cy3 replacements | | Cy3.5 |
| Cy3 replacements | | Cy5 |
| Backbone modifications | | di PS |
| 5' mods | | riboC for branch nm |
| Backbone modifications | | PNA |

TABLE 1-continued

GRON chemistries to be tested..

| Oligo type | | Modifications |
|---|---|---|
| Cy3 replacements | | DY647 |
| 5' mods | 5' branch | symmetric branch amidite/idC |

The foregoing modifications may also include known nucleotide modifications such as methylation, 5' intercalating dyes, modifications to the 5' and 3' ends, backbone modifications, crosslinkers, cyclization and 'caps' and substitution of one or more of the naturally occurring nucleotides with an analog such as inosine. Modifications of nucleotides include the addition of acridine, amine, biotin, cascade blue, cholesterol, Cy3@, Cy5@, Cy5.5@ Daboyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S", SE, BODIPY°, Marina Blue@, Pacific Blue@, Oregon Green@, Rhodamine Green@, Rhodamine Red@, Rhodol Green@ and Texas Red@. Polynucleotide backbone modifications include methylphosphonate, 2'-OMe-methylphosphonate RNA, phosphorothioate, RNA, 2'-OMeRNA. Base modifications include 2-amino-dA, 2-aminopurine, 3'-(ddA), 3'dA (cordycepin), 7-deaza-dA, 8-Br-dA, 8-oxo-dA, N6-Me-dA, abasic site (dSpacer), biotin dT, 2'-OMe-5Me-C, 2'-OMe-propynyl-C, 3'-(5-Me-dC), 3'-(ddC), 5-Br-dC, 5-1-duc, 5-Me-dC, 5-F-dC, carboxy-dT, convertible dA, convertible dC, convertible dG, convertible dT, convertible dU, 7-deaza-dG, 8-Br-dG, 8-oxo-dG, 06-Me-dG, S6-DNP-dG, 4-methyl-indole, 5-nitroindole, 2'-OMe-inosine, 2'-dI, o6-phenyl-dI, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, 04-Me-dT, 04-triazol dT, 2'-OMe-propynyl-U, 5-Br-dU, 2'-dU, 5-F-dU, 5-1-dU, 04-triazol dU. Said terms also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

Oligonucleobases may have nick(s), gap(s), modified nucleotides such as modified oligonucleotide backbones, abasic nucleotides, or other chemical moieties. In a further embodiment, at least one strand of the oligonucleobase includes at least one additional modified nucleotide, e.g., a 2'-O-methyl modified nucleotide such as a MOE (methoxyethyl), a nucleotide having a 5'-phosphorothioate group, a terminal nucleotide linked to a cholesteryl derivative, a 2'-deoxy-2'-fluoro modified nucleotide, a 2'-deoxy-modified nucleotide, a locked nucleotide, an abasic nucleotide (the nucleobase is missing or has a hydroxyl group in place thereof (see, e.g., Glen Research, http://www.glenresearch.com/GlenReports/GR21-14.html)), a 2'-amino-modified nucleotide, a 2'-alkyl-modified nucleotide, a morpholino nucleotide, a phosphoramidite, and a non-natural base comprising nucleotide. Various salts, mixed salts and free acid forms are also included.

Preferred modified oligonucleotide backbones include, for example, phosphorothioates, chiral phosphorothioates, phosphoro-dithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). The most common use of a linkage inversion is to add a 3'-3' linkage to the end of an antisense oligonucleotide with a phosphorothioate backbone. The 3'-3' linkage further stabilizes the antisense oligonucleotide to exonuclease degradation by creating an oligonucleotide with two 5'-OH ends and no 3'-OH end. Linkage inversions can be introduced into specific locations during oligonucleotide synthesis through use of "reversed phosphoramidites". These reagents have the phosphoramidite groups on the 5'-OH position and the dimethoxytrityl (DMT) protecting group on the 3'-OH position. Normally, the DMT protecting group is on the 5'-OH and the phosphoramidite is on the 3'-OH.

Examples of modified bases include, but are not limited to, 2-aminopurine, 2'-amino-butyryl pyrene-uridine, 2'-aminouridine, 2'-deoxyuridine, 2'-fluoro-cytidine, 2'-fluoro-uridine, 2,6-diaminopurine, 4-thio-uridine, 5-bromo-uridine, 5-fluoro-cytidine, 5-fluorouridine, 5-indo-uridine, 5-methyl-cytidine, inosine, N3-methyl-uridine, 7-deaza-guanine, 8-aminohexyl-amino-adenine, 6-thio-guanine, 4-thio-thymine, 2-thio-thymine, 5-iodo-uridine, 5-iodo-cytidine, 8-bromo-guanine, 8-bromo-adenine, 7-deaza-adenine, 7-diaza-guanine, 8-oxo-guanine, 5,6-dihydro-uridine, and 5-hydroxymethyl-uridine. These synthetic units are commercially available; (for example, purchased from Glen Research Company) and can be incorporated into DNA by chemical synthesis.

Examples of modification of the sugar moiety are 3'-deoxylation, 2'-fluorination, and arabanosidation, however, it is not to be construed as being limited thereto. Incorporation of these into DNA is also possible by chemical synthesis.

Examples of the 5' end modification are 5'-amination, 5'-biotinylation, 5'-fluoresceinylation, 5'-tetrafluoro-fluoreceinyaltion, 5'-thionation, and 5'-dabsylation, however it is not to be construed as being limited thereto.

Examples of the 3' end modification are 3'-amination, 3'-biotinylation, 2,3-dideoxidation, 3'-thionation, 3'-dabsylation, 3'-carboxylation, and 3'-cholesterylation, however, it is not to be construed as being limited thereto.

In one preferred embodiment, the oligonucleobase can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred reagents to make oligonucleobases are the reagents sold as Cy3™ and Cy5™ by Glen Research, Sterling Va. (now GE Healthcare), which are blocked phosphoroamidites that upon incorporation into an oligonucleotide yield 3,3,3',3'- tetramethyl N,N'-isopropyl substituted indomonocarbocyanine and indodicarbocyanine dyes, respectively. Cy3 is particularly preferred. When the indocarbocyanine is N-oxyalkyl substituted it can be conveniently linked to the 5' terminal of the oligodeoxynucleotide as a phosphodiester with a 5' terminal phosphate. When the commercially available Cy3 phosphoramidite is used as directed, the resulting 5' modification consists of a blocking substituent and linker together which are a N-hydroxypropyl, N'-phosphatidylpropyl 3,3,3',3'-tetramethyl indomonocarbocyanine. Other dyes contemplated include Rhodamine6G, Tetramethylrhodamine, Sulforhodamine 101, Merocyanine 540, Atto565, Atto550 26, Cy3.5, Dy547, Dy548, Dy549, Dy554, Dy555, Dy556, Dy560, mStrawberry and mCherry.

In a preferred embodiment the indocarbocyanine dye is tetra substituted at the 3 and 3' positions of the indole rings. Without limitations as to theory these substitutions prevent the dye from being an intercalating dye. The identity of the substituents at these positions is not critical.

The oligo designs herein described might also be used as more efficient donor templates in combination with other DNA editing or recombination technologies including, but not limited to, gene targeting using site-specific homologous recombination by zinc finger nucleases, Transcription Activator-Like Effector Nucleases (TALENs) or Clustered Regularly Interspaced Short Palindromic Repeats (CRISPRs).

The present invention generally relates to methods for the efficient modification of genomic cellular DNA and/or recombination of DNA into the genomic DNA of cells. Although not limited to any particular use, the methods of the present invention are useful in, for example, introducing a modification into the genome of a cell for the purpose of determining the effect of the modification on the cell. For example, a modification may be introduced into the nucleotide sequence which encodes an enzyme to determine whether the modification alters the enzymatic activity of the enzyme, and/or determine the location of the enzyme's catalytic region. Alternatively, the modification may be introduced into the coding sequence of a DNA-binding protein to determine whether the DNA binding activity of the protein is altered, and thus to delineate the particular DNA-binding region within the protein. Yet another alternative is to introduce a modification into a non-coding regulatory sequence (e.g., promoter, enhancer, regulatory RNA sequence (miRNA), etc.) in order to determine the effect of the modification on the level of expression of a second sequence which is operably linked to the non-coding regulatory sequence. This may be desirable to, for example, define the particular sequence which possesses regulatory activity.

One strategy for producing targeted gene disruption is through the generation of single strand or double strand DNA breaks caused by site-specific endonucleases. Endonucleases are most often used for targeted gene disruption in organisms that have traditionally been refractive to more conventional gene targeting methods, such as algae, plants, and large animal models, including humans. For example, there are currently human clinical trials underway involving zinc finger nucleases for the treatment and prevention of HIV infection. Additionally, endonuclease engineering is currently being used in attempts to disrupt genes that produce undesirable phenotypes in crops.

The homing endonucleases, also known as meganucleases, are sequence specific endonucleases that generate double strand breaks in genomic DNA with a high degree of specificity due to their large (e.g., >14 bp) cleavage sites. While the specificity of the homing endonucleases for their target sites allows for precise targeting of the induced DNA breaks, homing endonuclease cleavage sites are rare and the probability of finding a naturally occurring cleavage site in a targeted gene is low.

One class of artificial endonucleases is the zinc finger endonucleases. Zinc finger endonucleases combine a non-specific cleavage domain, typically that of FokI endonuclease, with zinc finger protein domains that are engineered to bind to specific DNA sequences. The modular structure of the zinc finger endonucleases makes them a versatile platform for delivering site-specific double-strand breaks to the genome. One limitation of the zinc finger endonucleases is that low specificity for a target site or the presence of multiple target sites in a genome can result in off-target cleavage events. As FokI endonuclease cleaves as a dimer, one strategy to prevent off-target cleavage events has been to design zinc finger domains that bind at adjacent 9 base pair sites.

TALENs are targetable nucleases are used to induce single- and double-strand breaks into specific DNA sites, which are then repaired by mechanisms that can be exploited to create sequence alterations at the cleavage site.

The fundamental building block that is used to engineer the DNA-binding region of TALENs is a highly conserved repeat domain derived from naturally occurring TALEs encoded by *Xanthomonas* spp. *proteobacteria*. DNA binding by a TALEN is mediated by arrays of highly conserved 33-35 amino acid repeats that are flanked by additional TALE-derived domains at the amino-terminal and carboxy-terminal ends of the repeats.

These TALE repeats specifically bind to a single base of DNA, the identity of which is determined by two hypervariable residues typically found at positions 12 and 13 of the repeat, with the number of repeats in an array corresponded to the length of the desired target nucleic acid, the identity of the repeat selected to match the target nucleic acid sequence. The target nucleic acid is preferably between 15 and 20 base pairs in order to maximize selectivity of the target site. Cleavage of the target nucleic acid typically occurs within 50 base pairs of TALEN binding. Computer programs for TALEN recognition site design have been described in the art. See, e.g., Cermak et al., Nucleic Acids Res. 2011 July; 39(12): e82.

Once designed to match the desired target sequence, TALENS can be expressed recombinantly and introduced into protoplasts as exogenous proteins, or expressed from a plasmid within the protoplast.

Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease.

Other DNA-modifying molecules may be used in targeted gene recombination. For example, peptide nucleic acids may be used to induce modifications to the genome of the target cell or cells (see, e.g., U.S. Pat. No. 5,986,053, to Ecker, herein incorporated by reference). In brief, synthetic nucleotides comprising, at least, a partial peptide backbone are used to target a homologous genomic nucleotide sequence.

Upon binding to the double-helical DNA, or through a mutagen ligated to the peptide nucleic acid, modification of the target DNA sequence and/or recombination is induced to take place. Targeting specificity is determined by the degree of sequence homology between the targeting sequence and the genomic sequence.

Furthermore, the present invention is not limited to the particular methods which are used herein to execute modification of genomic sequences. Indeed, a number of methods are contemplated. For example, genes may be targeted using triple helix forming oligonucleotides (TFO). TFOs may be generated synthetically, for example, by PCR or by use of a gene synthesizer apparatus. Additionally, TFOs may be isolated from genomic DNA if suitable natural sequences are found. TFOs may be used in a number of ways, including, for example, by tethering to a mutagen such as, but not limited to, psoralen or chlorambucil (see, e.g., Havre et al., Proc Nat'l Acad Sci, U.S.A. 90:7879-7883, 1993; Havre et al., J Virol 67:7323-7331, 1993; Wang et al., Mol Cell Biol 15:1759-1768, 1995; Takasugi et al., Proc Nat'l Acad Sci, U.S.A. 88:5602-5606, 1991; Belousov et al., Nucleic Acids Res 25:3440-3444, 1997). Furthermore, for example, TFOs may be tethered to donor duplex DNA (see, e.g., Chan et al., J Biol Chem 272:11541-11548, 1999). TFOs can also act by binding with sufficient affinity to provoke error-prone repair (Wang et al., Science 271:802-805, 1996).

The invention's methods are not limited to the nature or type of DNA-modifying reagent which is used. For example, such DNA-modifying reagents release radicals which result in DNA strand breakage. Alternatively, the reagents alkylate DNA to form adducts which would block replication and transcription. In another alternative, the reagents generate crosslinks or molecules that inhibit cellular enzymes leading to strand breaks. Examples of DNA-modifying reagents which have been linked to oligonucleotides to form TFOs include, but are not limited to, indolocarbazoles, napthalene diimide (NDI), transplatin, bleomycin, analogues of cyclopropapyrroloindole, and phenanthodihydrodioxins. In particular, indolocarbazoles are topoisomerase I inhibitors. Inhibition of these enzymes results in strand breaks and DNA protein adduct formation [Arimondo et al., Bioorganic and Medicinal Chem. 8, 777, 2000]. NDI is a photooxidant that can oxidize guanines which could cause mutations at sites of guanine residues [Nunez, et al., Biochemistry, 39, 6190, 2000]. Transplatin has been shown to react with DNA in a triplex target when the TFO is linked to the reagent. This reaction causes the formation of DNA adducts which would be mutagenic [Columbier, et al., Nucleic Acids Research, 24: 4519, 1996]. Bleomycin is a DNA breaker, widely used as a radiation mimetic. It has been linked to oligonucleotides and shown to be active as a breaker in that format [Sergeyev, Nucleic Acids Research 23, 4400, 1995; Kane, et al., Biochemistry, 34, 16715, 1995]. Analogues of cyclopropapyrroloindole have been linked to TFOs and shown to alkylate DNA in a triplex target sequence. The alkylated DNA would then contain chemical adducts which would be mutagenic [Lukhtanov, et al., Nucleic Acids Research, 25, 5077, 1997]. Phenanthodihydrodioxins are masked quinones that release radical species upon photoactivation. They have been linked to TFOs and have been shown to introduce breaks into duplex DNA on photoactivation [Bendinskas et al., Bioconjugate Chem. 9, 555, 1998].

Other methods of inducing modifications and/or recombination are contemplated by the present invention. For example, another embodiment involves the induction of homologous recombination between an exogenous DNA fragment and the targeted gene (see e.g., Capecchi et al., Science 244:1288-1292, 1989) or by using peptide nucleic acids (PNA) with affinity for the targeted site. Still other methods include sequence specific DNA recognition and targeting by polyamides (see e.g., Dervan et al., Curr Opin Chem Biol 3:688-693, 1999; Biochemistry 38:2143-2151, 1999) and the use nucleases with site specific activity (e.g., zinc finger proteins, TALENs, Meganucleases and/or CRISPRs).

The present invention is not limited to any particular frequency of modification and/or recombination. The invention's methods result in a frequency of modification in the target nucleotide sequence of from 0.2% to 3%. Nonetheless, any frequency (i.e., between 0% and 100%) of modification and/or recombination is contemplated to be within the scope of the present invention. The frequency of modification and/or recombination is dependent on the method used to induce the modification and/or recombination, the cell type used, the specific gene targeted and the DNA mutating reagent used, if any. Additionally, the method used to detect the modification and/or recombination, due to limitations in the detection method, may not detect all occurrences of modification and/or recombination. Furthermore, some modification and/or recombination events may be silent, giving no detectable indication that the modification and/or recombination has taken place. The inability to detect silent modification and/or recombination events gives an artificially low estimate of modification and/or recombination. Because of these reasons, and others, the invention is not limited to any particular modification and/or recombination frequency. In one embodiment, the frequency of modification and/or recombination is between 0.01% and 100%. In another embodiment, the frequency of modification and/or recombination is between 0.01% and 50%. In yet another embodiment, the frequency of modification and/or recombination is between 0.1% and 10%. In still yet another embodiment, the frequency of modification and/or recombination is between 0.1% and 5%.

The term "frequency of mutation" as used herein in reference to a population of cells which are treated with a DNA-modifying molecule that is capable of introducing a mutation into a target site in the cells' genome, refers to the number of cells in the treated population which contain the mutation at the target site as compared to the total number of cells which are treated with the DNA-modifying molecule. For example, with respect to a population of cells which is treated with the DNA-modifying molecule TFO tethered to psoralen which is designed to introduce a mutation at a target site in the cells' genome, a frequency of mutation of 5% means that of a total of 100 cells which are treated with TFO-psoralen, 5 cells contain a mutation at the target site.

Although the present invention is not limited to any degree of precision in the modification and/or recombination of DNA in the cell, it is contemplated that some embodiments of the present invention require higher degrees of precision, depending on the desired result. For example, the specific sequence changes required for gene repair (e.g., particular base changes) require a higher degree of precision as compared to producing a gene knockout wherein only the disruption of the gene is necessary. With the methods of the present invention, achievement of higher levels of precision in modification and/or homologous recombination techniques is greater than with prior art methods.

Delivery of Gene Repair Oligonucleobases into Plant Cells

Any commonly known method used to transform a plant cell can be used for delivering the gene repair oligonucleobases. Illustrative methods are listed below. The present invention contemplates many methods to transfect the cells with the DNA-modifying reagent or reagents. Indeed, the present invention is not limited to any particular method. Methods for the introduction of DNA modifying reagents into a cell or cells are well known in the art and include, but are not limited to, microinjection, electroporation, passive adsorption, calcium phosphate-DNA co-precipitation, DEAE-dextran-mediated transfection, polybrene-mediated transfection, liposome fusion, lipofectin, nucleofection, protoplast fusion, retroviral infection, biolistics (i.e., particle bombardment) and the like.

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204,253 describe general techniques for selecting microcarriers and devices for projecting them.

Specific conditions for using microcarriers in the methods of the present invention are described in International Publication WO 99/07865. In an illustrative technique, ice cold microcarriers (60 mg/mL), mixed duplex oligonucleotide (60 mg/mL) 2.5 M $CaCl_2$) and 0.1 M spermidine are added in that order; the mixture gently agitated, e.g., by vortexing, for 10 minutes and then left at room temperature for 10 minutes, whereupon the microcarriers are diluted in 5 volumes of ethanol, centrifuged and resuspended in 100% ethanol. Good results can be obtained with a concentration in the adhering solution of 8-10 μg/μL microcarriers, 14-17 μg/mL mixed duplex oligonucleotide, 1.1-1.4 M $CaCl_2$) and 18-22 mM spermidine. Optimal results were observed under the conditions of 8 μg/μL microcarriers, 16.5 μg/mL mixed duplex oligonucleotide, 1.3 M $CaCl_2$) and 21 mM spermidine.

Gene repair oligonucleobases can also be introduced into plant cells for the practice of the present invention using microfibers to penetrate the cell wall and cell membrane. U.S. Pat. No. 5,302,523 to Coffee et al describes the use of silicon carbide fibers to facilitate transformation of suspension maize cultures of Black Mexican Sweet. Any mechanical technique that can be used to introduce DNA for transformation of a plant cell using microfibers can be used to deliver gene repair oligonucleobases for transmutation.

An illustrative technique for microfiber delivery of a gene repair oligonucleobase is as follows: Sterile microfibers (2 μg) are suspended in 150 μL of plant culture medium containing about 10 μg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 h as is appropriate for the particular trait.

In an alternative embodiment, the gene repair oligonucleobases can be delivered to the plant cell by electroporation of a protoplast derived from a plant part. The protoplasts are formed by enzymatic treatment of a plant part, particularly a leaf, according to techniques well known to those skilled in the art. See, e.g., Gallois et al, 1996, in Methods in Molecular Biology 55:89-107, Humana Press, Totowa, N.J.; Kipp et al., 1999, in Methods in Molecular Biology 133: 213-221, Humana Press, Totowa, N.J. The protoplasts need not be cultured in growth media prior to electroporation. Illustrative conditions for electroporation are 3. times. 10.sup.5 protoplasts in a total volume of 0.3 mL with a concentration of gene repair oligonucleobase of between 0.6-4 μg/mL.

In an alternative embodiment, nucleic acids are taken up by plant protoplasts in the presence of the membrane-modifying agent polyethylene glycol, according to techniques well known to those skilled in the art. In another alternative embodiment, the gene repair oligonucleobases can be delivered by injecting it with a microcapillary into plant cells or into protoplasts.

In an alternative embodiment, nucleic acids are embedded in microbeads composed of calcium alginate and taken up by plant protoplasts in the presence of the membrane-modifying agent polyethylene glycol (see, e.g., Sone et al., 2002, Liu et al., 2004).

In an alternative embodiment, nucleic acids forzen in water and introduced into plant cells by bombardment in the form of microparticles (see, e.g., Gilmore, 1991, U.S. Pat. No. 5,219,746; Brinegar et al.).

In an alternative embodiment, nucleic acids attached to nanoparticles are introduced into intact plant cells by incubation of the cells in a suspension containing the nanoparticle the (see, e.g., Pasupathy et al., 2008) or by delivering them into intact cells through particle bombardment or into protoplasts by co-incubation (see, e.g., Torney et al., 2007).

In an alternative embodiment, nucleic acids complexed with penetrating peptides and delivered into cells by co-incubation (see, e.g., Chugh et al., 2008, WO 2008148223 A1; Eudes and Chugh.

In an alternative embodiment, nucleic acids are introduced into intact cells through electroporation (see, e.g., He et al., 1998, US 2003/0115641 A1, Dobres et al.).

In an alternative embodiment, nucleic acids are delivered into cells of dry embryos by soaking them in a solution with nucleic acids (by soaking dry embryos in (see, e.g., Topfer et al., 1989, Senaratna et al., 1991).

Selection of Plants

In various embodiments, plants as disclosed herein can be of any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the plant maybe selected from a species of plant from the group consisting of canola, sunflower, corn, tobacco, sugar beet, cotton, maize, wheat, barley, rice, alfalfa, barley, sorghum, tomato, mango, peach, apple, pear, strawberry, banana, melon, potato, carrot, lettuce, onion, soy bean, soya spp, sugar cane, pea, chickpea, field pea, faba bean, lentils, turnip, rutabaga, brussel sprouts, lupin, cauliflower, kale, field beans, poplar, pine, *eucalyptus*, grape, citrus, triticale, alfalfa, rye, oats, turf and forage grasses, flax, oilseed rape, mustard, cucumber, morning glory, balsam, pepper, eggplant, marigold, lotus, cabbage, daisy, carnation, tulip, iris, lily, and nut producing plants insofar as they are not already specifically mentioned.

Plants and plant cells can be tested for resistance or tolerance to an herbicide using commonly known methods in the art, e.g., by growing the plant or plant cell in the presence of an herbicide and measuring the rate of growth as compared to the growth rate in the absence of the herbicide.

As used herein, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild-type AHAS protein.

As used herein, substantially normal development of a plant, plant organ, plant tissue or plant cell is defined as the occurrence of one or more development events in the plant, plant organ, plant tissue or plant cell that are substantially the same as those occurring in a corresponding plant, plant organ, plant tissue or plant cell expressing the wild-type protein.

In certain embodiments plant organs provided herein include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants are substantially "tolerant" to a relevant herbicide when they are subjected to it and provide a dose/response curve which is shifted to the right when compared with that provided by similarly subjected non-tolerant like plant. Such dose/response curves have "dose" plotted on the X-axis and "percentage kill", "herbicidal effect", etc., plotted on the y-axis. Tolerant plants will require more herbicide than non-tolerant like plants in order to produce a given herbicidal effect. Plants that are substantially "resistant" to the herbicide exhibit few, if any, necrotic, lytic, chlorotic or other lesions, when subjected to herbicide at concentrations and rates which are typically employed by the agrochemical community to kill weeds in the field. Plants which are resistant to an herbicide are also tolerant of the herbicide.

Generation of Plants

Tissue culture of various tissues of plant species and regeneration of plants therefrom is known. For example, the propagation of a canola cultivar by tissue culture is described in any of the following but not limited to any of the following: Chuong et al., "A Simple Culture Method for *Brassica* hypocotyls Protoplasts," Plant Cell Reports 4:4-6, 1985; Barsby, T. L., et al., "A Rapid and Efficient Alternative Procedure for the Regeneration of Plants from Hypocotyl Protoplasts of *Brassica napus*," Plant Cell Reports (Spring, 1996); Kartha, K., et al., "In vitro Plant Formation from Stem Explants of Rape," Physiol. Plant, 31:217-220, 1974; Narasimhulu, S., et al., "Species Specific Shoot Regeneration Response of Cotyledonary Explants of Brassicas," Plant Cell Reports (Spring 1988); Swanson, E., "Microspore Culture in *Brassica*," Methods in Molecular Biology, Vol. 6, Chapter 17, p. 159, 1990.

Further reproduction of the variety can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybeans," Crop Sci. 31:333-337, 1991; Stephens, P. A., et al., "Agronomic Evaluation of Tissue-Culture-Derived Soybean Plants," Theor. Appl. Genet. 82:633-635, 1991; Komatsuda, T. et al., "Maturation and Germination of Somatic Embryos as Affected by Sucrose and Plant Growth Regulators in Soybeans *Glycine gracilis* Skvortz and *Glycine max* (L.) Merr." Plant Cell, Tissue and Organ Culture, 28:103-113, 1992; Dhir, S. et al., "Regeneration of Fertile Plants from Protoplasts of Soybean (*Glycine max* L. Merr.); Genotypic Differences in Culture Response," Plant Cell Reports 11:285-289, 1992; Pandey, P. et al., "Plant Regeneration from Leaf and Hypocotyl Explants of *Glycine wightii* (W. and A.) VERDC. var. *longicauda*," Japan J. Breed. 42:1-5, 1992; and Shetty, K., et al., "Stimulation of In Vitro Shoot Organogenesis in *Glycine max* (Merrill.) by Allantoin and Amides," Plant Science 81:245-251, 1992. The disclosures of U.S. Pat. No. 5,024,944 issued Jun. 18, 1991 to Collins et al., and U.S. Pat. No. 5,008,200 issued Apr. 16, 1991 to Ranch et al., are hereby incorporated herein in their entirety by reference.

EXAMPLES

Example 1: GRON Length

Sommer et al., (Mol Biotechnol. 33:115-22, 2006) describes a reporter system for the detection of in vivo gene conversion which relies upon a single nucleotide change to convert between blue and green fluorescence in green fluorescent protein (GFP) variants. This reporter system was adapted for use in the following experiments using *Arabidopsis thaliana* as a model species in order to assess efficiency of GRON conversion following modification of the GRON length.

In short, for this and the subsequent examples an *Arabidopsis* line with multiple copies of a blue fluorescent protein gene was created by methods known to those skilled in the art (see, e.g., Clough and Brent, 1998). Root-derived meristematic tissue cultures were established with this line, which was used for protoplast isolation and culture (see, e.g., Mathur et al., 1995). GRON delivery into protoplasts was achieved through polyethylene glycol (PEG) mediated GRON uptake into protoplasts. A method using a 96-well format, similar to that described by similar to that described by Fujiwara and Kato (2007) was used. In the following the protocol is briefly described. The volumes given are those applied to individual wells of a 96-well dish.

1. Mix 6.25 µl of GRON (80 µM) with 25 µl of *Arabidopsis* BFP transgenic root meristematic tissue-derived protoplasts at $5 \times 10^6$ cells/ml in each well of a 96 well plate.

2. 31.25 µl of a 40% PEG solution was added and the protoplasts were mixed.

3. Treated cells were incubated on ice for 30 min.

4. To each well 200 µl of W5 solution was added and the cells mixed.

5. The plates were allowed to incubate on ice for 30 min allowing the protoplasts to settle to the bottom of each well.

6. 200 µl of the medium above the settled protoplasts was removed.

7. 85 µl of culture medium (MSAP, see Mathur et al., 1995) was added.

8. The plates were incubated at room temperate in the dark for 48 hours. The final concentration of GRON after adding culture medium is 8 µM.

Forty eight hours after GRON delivery samples were analyzed by flow cytometry in order to detect protoplasts whose green and yellow fluorescence is different from that of control protoplasts (BFP0 indicates non-targeting GRONs with no change compared to the BFP target; C is the coding strand design and NC is the non-coding strand design). A single C to T nucleotide difference (coding strand) or G to A nucleotide targeted mutation (non-coding strand) in the center of the BFP4 molecules. The green fluorescence is caused by the introduction of a targeted mutation in the BFP gene, resulting in the synthesis of GFP. The results are shown in FIG. 1.

The following table shows the sequence of exemplary 101-mer and 201-mer BFP4/NC 5'-3PS/3'-3PS GRONs designed for the conversion of a blue fluorescent protein (BFP) gene to green fluorescence. (3PS indicates 3 phosphothioate linkages at each of the 5' and 3' oligo ends).

TABLE 1

| SEQ ID NO | GRON Name | GRON Nucleotide Sequence |
|---|---|---|
| 1 | BFP4/NC 101-mer | G* T*C*G TGC TGC TTC ATG TGG TCG GGG TAG CGG CTG AAG CAC TGC ACG CCG TAG GTG AAG GTG GTC ACG AGG GTG GGC CAG GGC ACG GGC AGC TTG CCG G*T*G* G |
| 2 | BFP0/NC 101-mer | G* T*C*G TGC TGC TTC ATG TGG TCG GGG TAG CGG CTG AAG CAC TGC ACG CCG TGG GTG AAG GTG GTC ACG AGG GTG GGC CAG GGC ACG GGC AGC TTG CCG G*T*G *G |
| 3 | BFP4/C 101-mer | C *C*A*C CGG CAA GCT GCC CGT GCC CTG GCC CAC CCT CGT GAC CAC CTT CAC CTA CGG CGT GCA GTG CTT CAG CCG CTA CCC CGA CCA CAT GAA GCA GCA C*G*A*C |
| 4 | BFP0/C 101-mer | C*C*A*CCGGCAAGCTGCCCGTGCCCTGGCCCACCCT CGTGACCACCTTCACCCACGGCGTGCAGTGCTTCAGC CGCTACCCCGACCACATGAAGCAGCAC*G*A*C |
| 5 | BFP4/NC 201-mer | A*A*G*ATGGTGCGCTCCTGGACGTAGCCTTCGGGCA TGGCGGACTTGAAGAAGTCGTGCTGCTTCATGTGGTC TGGGTAGCGGCTGAAGCACTGCACGCCGTAGGTGAAG GTGGTCACGAGGGTGGGCCAGGGCACGGGCAGCTTGC CGGTGGTGCAGATGAACTTCAGGGTCAGCTTGCCG TAGGTGGCATCGCCCTCG *C*C*C |
| 6 | BFP0/NC 201-mer | A*A*G*ATGGTGCGCTCCTGGACGTAGCCTTCGGGCA TGGCGGACTTGAAGAAGTCGTGCTGCTTCATGTGGTC GGGGTAGCGGCTGAAGCACTGCACGCCGTGGGTGAAG GTGGTCACGAGGGTGGGCCAGGGCACGGGCAGCTTGC CGGTGGTGCAGATGAACTTCAGGGTCAGCTTGCCG TAGGTGGCATCGCCCTCG *C*C*C |
| 7 | BFP4/C 201-mer | G*G*G*CGAGGGCGATGCCACCTACGGCAAGCTGACC CTGAAGTTCATCTGCACCACCGGCAAGCTGCCCGTGC CCTGGCCCACCCTCGTGACCACCTTCACCTACGGCGT GCAGTGCTTCAGCCGCTACCCCGACCACATGAAGCAG CACGACTTCTTCAAGTCCGCCATGCCCGAAGGCTACG TCCAGGA GCGCACCAT *C*T*T |
| 8 | BFP0/C 201-mer | G*G*G*CGAGGGCGATGCCACCTACGGCAAGCTGACC CTGAAGTTCATCTGCACCACCGGCAAGCTGCCCGTGC CCTGGCCCACCCTCGTGACCACCTTCACCCACGGCGT GCAGTGCTTCAGCCGCTACCCCGACCACATGAAGCAG CACGACTTCTTCAAGTCCGCCATGCCCGAAGGCTACG TCCAGGA GCGCACCAT*C*T*T |

* = PS linkage (phosphothioate)

Example 2: Conversion Rates Using 5'Cy3/3'idC Labeled GRONs

The purpose of this series of experiments is to compare the efficiencies of phosphothioate (PS) labeled GRONs (having 3 PS moieties at each end of the GRON) to the 5'Cy3/3'idC labeled GRONs. The 5'Cy3/3'idC labeled GRONs have a 5' Cy3 fluorophore (amidite) and a 3' idC reverse base. Efficiency was assessed using conversion of blue fluorescent protein (BFP) to green fluorescence In all three experiments, done either by PEG delivery of GRONs into protoplasts in individual Falcon tubes (labeled "Tubes") or in 96-well plates (labeled "96-well dish"), there was no significant difference between the different GRON chemistries in BFP to GFP conversion efficiency as determined by cytometry (FIG. 1).

Example 3: Comparison Between the 41-Mer BFP4/NC 5'-3PS/3'-3PS GRON and Okazaki Fragment GRONs The purpose of this series of experiments is to compare the conversion efficiencies of the phosphothioate (PS) labeled GRONs with 3PS moieties at each end of the GRON to "Okazaki fragment GRONs" in the presence and absence of a member of the bleomycin family, Zeocin™ (1 mg/ml) to induce DNA breaks. The design of these GRONs are depicted in FIG. 2. GRONs were delivered into *Arabidopsis* BFP protoplasts by PEG treatment and BFP to GFP conversion was determined at 24 h post treatment by cytometry. Samples treated with zeocin (1 mg/ml) were incubated with zeocin for 90 min on ice prior to PEG treatment.

In general the presence of zeocin (1 mg/ml) increased BFP to GFP conversion as determined by cytometry (Table 2). In both the presence and absence of zeocin, the NC Okazaki GRON containing one 2'-O Me group on the first RNA base at the 5' end of the GRON was more efficacious at converting BFP to GFP when compared to the NC Okazaki GRON containing one 2'-O Me group on each of the first nine 5' RNA bases (FIG. 2 and Table 2).

In all experiments, there was no significant difference between the 41-mer BFP4/NC 5'3PS/3'3PS and the 71-mer Okazaki Fragment BFP4/NC GRON that contains one 5' 2'-O me group on the first 5' RNA base (denoted as BFP4 71-mer (1) NC) in BFP to GFP conversion in both the presence or absence of 1 mg/ml of zeocin as determined by cytometry (FIG. 2 and Table 2). It is important to note that in the presence of zeocin (and expected for bleomycin, phleomycin, tallysomycin, pepleomycin and other members of this family of antibiotics) that conversion becomes strand independent (i.e., both C and NC GRONs with the designs tested in these experiments display approximately equal activity).

TABLE 2

Comparison of a standard GRON design with Okazaki fragment GRON designs in the presence and absence of a glycopeptide antibiotic zeocin.

| Exp. | BFP4 41-mer | | BFP4 71-mer (0) | | BFP4 71-mer (1) | | BFP4 71-mer (9) | |
|---|---|---|---|---|---|---|---|---|
| Name | NC | C | NC | C | NC | C | NC | C |
| | Zeocin (+) | | | | | | | |
| APT043 | 0.13 | 0.0875 | 0.2275 | 0.2075 | 0.355 | 0.2275 | 0.2325 | 0.195 |
| APT066 | 1.9 | 0.713 | 0.762 | 0.683 | 1.318 | 0.7103 | 0.769 | 0.883 |
| Mean | 1.015 | 0.40025 | 0.49475 | 0.44525 | 0.8365 | 0.4689 | 0.50075 | 0.539 |
| Std Dev | 1.251579 | 0.442295 | 0.377949 | 0.336229 | 0.680944 | 0.341391 | 0.379363 | 0.486489 |
| SE | 0.885134 | 0.312797 | 0.26729 | 0.237786 | 0.481573 | 0.241436 | 0.268291 | 0.344052 |

TABLE 2-continued

Comparison of a standard GRON design with Okazaki fragment GRON designs in the presence and absence of a glycopeptide antibiotic zeocin.

Zeocin (−)

| APT043 | nd | nd | 0.1875 | 0.0175 | 0.21 | 0.025 | 0.1 | 0.0225 |
|---|---|---|---|---|---|---|---|---|
| APT066 | 0.109 | 0.007 | 0.112 | 0.005 | 0.141 | 0.023 | 0.065 | 0.021 |
| Mean | 0.109 | 0.007 | 0.14975 | 0.01125 | 0.1755 | 0.024 | 0.0825 | 0.02175 |
| Std Dev | na | na | 0.053387 | 0.008839 | 0.04879 | 0.001414 | 0.024749 | 0.001061 |
| SE | na | na | 0.037756 | 0.006251 | 0.034505 | 0.001 | 0.017503 | 0.00075 |

| | |
|---|---|
| BFP4 71-mer (0) NC C | 5' first 10 bp are RNA and GRON has no protection |
| BFP4 71-mer (1) NC C | 5' first 10 bp are RNA and first bp on the 5' end has a 2' O-Me |
| BFP4 71-mer (9) NC C | 5' first 10 bp are RNA and first nine bp on the 5' end has a 2' O-Me |

Example 4: Comparison Between the 41-Mer, 101-Mer and 201-Mer BFP4/NC 5'-3PS/3'-3PS GRONs The purpose of this series of experiments was to compare the conversion efficiencies (in the presence and absence of zeocin) of the phosphothioate (PS) labeled GRONs with 3PS moieties at each end of the GRON of different lengths: 41-mer, 101-mer and 201-mer shown in Table 1. Again, the presence of zeocin (1 mg/ml) increased BFP to GFP conversion rates as determined by cytometry (Table 3). The overall trend in all three experiments was linear with increasing NC GRON length in both the presence and absence of zeocin. Except for the BFP-4/NC/101 and BFP-4/C/101 in the presence of zeocin, this had conversion rates that were close to equal but lower than the 41-mer NC GRON. This is in contrast to all previous experiments in which the BFP-4/41 coding and non-coding GRONs were used, wherein the non-coding was always far superior to the coding GRON. This asymmetry in conversion frequency also applies to the BFP-4/201 GRONs used in this experimental series.

Example 5: CRISPRs Combined with GRONs to Improve Conversion in Plants

Three design components must be considered when assembling a CRISPR complex: Cas9, gRNA (guide RNA) and the target region (proto-spacer in endogenous target gene).

Cas 9
Transient expression of Cas9 gene from *Streptococcus pyogenes* codon optimized for *Arabidopsis* or corn driven by 35S or corn ubiquitin respectively. Optimized genes synthesized by Genewiz or DNA 2.0. NB must ensure no cryptic introns are created.
RBCSE9 terminator as per G1155
Single SV40 NLS (PKKRKV) (SEQ ID NO: 9) as a C-terminal fusion
The vector backbone would be as per all our transient expression systems—G1155.
gRNA
Propose to use a chimeric tracrRNA—pre-creRNA as per Le Cong et al., 2013 and Jinek et al., 2013. Note that LeCong et al. showed that the native full length tracr+ pre-crRNA complex cleaved much more efficiently than the chimeric version. An option therefore would be to make a chimera using the full length (89 bp) tracrRNA.

TABLE 3

| | BFP4 41-mer | | BFP4 101-mer | | BFP4 201-mer | |
|---|---|---|---|---|---|---|
| Exp. Name | NC | C | NC | C | NC | C |
| Zeocin (+) | | | | | | |
| APT038 | 0.2425 | 0.1275 | 0.3025 | 0.2575 | 0.97 | 0.245 |
| APT043 | 0.13 | 0.0875 | 0.185 | 0.2275 | 0.66 | 0.1875 |
| APT047 | 0.3975 | 0.145 | 0.19 | 0.125 | 0.235 | 0.085 |
| APT052 | 0.3275 | nd | 0.17 | 0.21 | 0.585 | 0.225 |
| APT052 | nd | nd | 0.3225 | 0.3175 | 0.5075 | 0.3125 |
| APT058 | 1.4275 | nd | 1.2 | nd | 1.9 | nd |
| APT066 | 1.9 | 0.713 | 0.992 | 1.05 | 1.7 | 0.916 |
| Mean | 0.7375 | 0.26825 | 0.4802857 | 0.3645833 | 0.9367857 | 0.3285 |
| Std Dev | 0.738280096 | 0.2974751 | 0.4289679 | 0.3416336 | 0.6309429 | 0.2974122 |
| SE | 0.30146186 | 0.1487375 | 0.1621194 | 0.1394992 | 0.2384516 | 0.1214423 |
| Zeocin (−) | | | | | | |
| APT038 | 0.05 | 0.01 | 0.1025 | 0.025 | 0.5725 | 0.025 |
| APT066 | 0.109 | 0.007 | 0.214 | 0.047 | 0.566 | 0.035 |
| Mean | 0.0795 | 0.0085 | 0.15825 | 0.036 | 0.56925 | 0.03 |
| Std Dev | 0.0417193 | 0.0021213 | 0.0788424 | 0.0155563 | 0.0045962 | 0.0070711 |
| SE | 0.029504456 | 0.0015002 | 0.0557584 | 0.0110017 | 0.0032505 | 0.0050008 |

Sequence of gRNA ((N)$_{20}$ represents guide sequence). The bracketed sequence comprises the full length 89 bp form.

(SEQ ID NO: 10)
NNNNNNNNNNNNNNNNNNNNGTTTTAGAGCTAGAAATAGCAAGTTAAAAT

AAGGCTAGTCCG(TTATGTTCTTGAAAAAAGTGAGTGGCACCGAGTCGGT

GGTGCTTTTTT)

Figure 3:
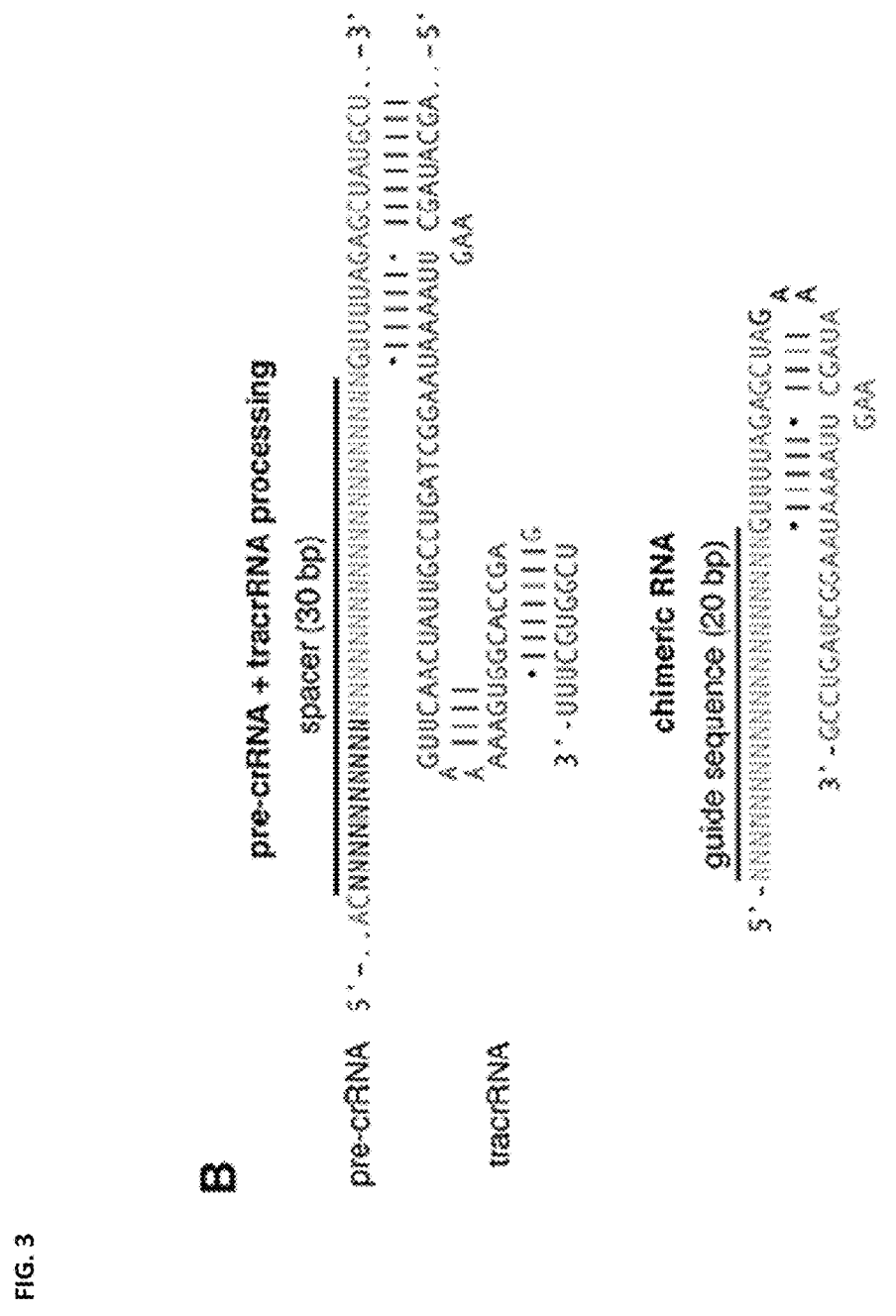

FIG. 3, from LeCong et al., shows the native complex and the chimera (SEQ ID NOS: 11, 12, and 13).

The gRNA would be expressed under the AtU6 RNA pol III promoter in *Arabidopsis* (sequence given below). In corn the ZmU6 RNA pol III promoter could be used. These choices are based on Wang et al. 2008.

RBCSE9 terminator as per G1155 or a string of T's as per Wang et al. 2013 and the one-component approach shown below.

At U6 Promoter Sequence from Wang et al

Target Region

The guide sequence specificity is defined by the target region sequence. Irrespective of the choice of model organism this will be the Y66H locus of BFP. A PAM (NGG) sequence in the vicinity of Y66H is the only design restriction. Also, including the Y66H position in the 3' 12 bp of the guide sequence ("seed sequence") would mean that once repair has been achieved the site will not get re-cut.

```
Tc gtg acc acc ttc acc cac ggc   (SEQ ID NO: 14)
   V   T   T   F   T   Y
 G
    61  62  63  64  65 66 67    (SEQ ID NO: 15)
```

A distinct vector backbone from G1155 will be needed in order to enable co-delivery of Cas9 and gRNA. This problem will be circumvented with the one-component approach:

One Component Approach

Le Cong et al. (2013) used a simplified approach, expressing both the gRNA and the Cas9 as a single transient construct, driven by the pol III U6 promoter, as outlined below. In this way, for a given crop, multiple genes could be targeted by simply swapping in the guide insert sequence. We would replace the EF1α promoter for one suitable for the crop (pMAS for At, Ubi for Zm). For the terminator we would use RBCSE9. The NLS used in plants would be a single C-terminal SV40 as outlined above.

Note that in the construct below a truncated gRNA is used where the tracer RNA region is not included. The authors showed that in humans that this was less effective at guiding the Cas9 that the full length version. It is therefore proposed that the full length gRNA to be used here. Notably in a subsequent paper using CRISPRs in yeast, DiCarlo et al. (2013) used the full length version. The cassette would be cloned into a G1155 background (SEQ ID NO: 16-19).

Schematic of the expression vector for chimeric crRNA. The guide sequence can be inserted between two BbsI sites using annealed oligonucleotides. The vector already contains the partial direct repeat (gray) and partial tracrRNA (red) sequences. WPRE, Woodchuck hepatitis virus post transcriptional regulatory element.

In Vivo Assay

Transient Option

One approach to confirm target recognition and nuclease activity in planta would be to emulate the YFP single stranded annealing assay which Zhang et al. (2013) used for TALENs. The spacer sequence (target sequence) plus PAM would need to be inserted into the YFP or equivalent gene.

Transient Option

The TALEN—BFP system could be used as a control.

Whilst the above approach would be an on-going tool for confirming functionality of a given CRISPR system for a given spacer sequence, proof of concept of the activity of CRISPRs in plants would be to use the GFP system.

Here the designs used for BFP→GFP could be co-transformed into At together with G1155 and no GRON. If cutting were efficient enough, a reduction in GFP expression could be apparent. This would likely require optimization of plasmid loading.

Once activity is confirmed a genomic BFP target would be targeted with a visual and sequence-based read-out.

In Vitro Assay

In order to rapidly confirm activity of a CRISPR system, an in vitro assay could be used as per Jinek et al 2012. Here a pre-made and purified *S.pyogenes* Cas9 is incubated with synthesized gRNA and a plasmid containing the recognition sequence. Successful cleavage is analysed by gel electrophoresis to look for cut plasmids. Detailed protocol:

Plasmid DNA cleavage assay. Synthetic or in vitro-transcribed tracrRNA and crRNA were pre-annealed prior to the reaction by heating to 95° C. and slowly cooling down to room temperature. Native or restriction digest-linearized plasmid DNA (300 ng (~8 nM)) was incubated for 60 min at 37° C. with purified Cas9 protein (50-500 nM) and tracrRNA:crRNA duplex (50-500 nM, 1:1) in a Cas9 plasmid cleavage buffer (20 mM HEPES pH 7.5, 150 mM KCl, 0.5 mM DTT, 0.1 mM EDTA) with or without 10 mM MgCl2. The reactions were stopped with 5×DNA loading buffer containing 250 mM EDTA, resolved by 0.8 or 1% agarose gel electrophoresis and visualized by ethidium bromide staining. For the Cas9 mutant cleavage assays, the reactions were stopped with 5×SDS loading buffer (30% glycerol, 1.2% SDS, 250 mM EDTA) prior to loading on the agarose gel.

Trait Targets in Crops

Given the flexibility of the CRISPR recognition sequence it is not difficult to find potential protospacer sequences as defined by a 3' NGG PAM sequence.

ZmEPSPS

The example below shows a suitable protospacer sequence (yellow) and PAM (blue) in order to create a DS break in the catalytic site of ZmEPSPS where mutations at the T97 and P101 are known to cause glyphosate tolerance. Subsequent oligo-mediated repair (ODM) of the break would result in the desired changes (SEQ ID NO: 20 and 21).

```
  T   A   M   R   P   L T   V   A
act gca atg cgg cca ttg aca gca gct gtt act gct A   V
gct gg
```

The table below gives the protospacer sequences of genes of interest in crops of interest:

| Crop | Gene | Protospacer Sequence | SEQ ID NO |
|---|---|---|---|
| Canola | EPSPS 2-22 P101 | ccgctgccgttactgctgca | 22 |
| | EPSPS - 2-23 P101 | cggctgcagttactgctgct | 23 |
| | EPSPS 2-25 P101* | ccgctgccgttactgctgca | 24 |
| | EPSPS 2-28 P101 | ccgctgcagttacagctgca | 25 |
| Flax | EPSPS P101 | cagctgctgtaacagccgct | 26 |
| Potato | EPSPS - 2.1/2:2/2 P101 | cagcagcagttgctgtagct | 27 |
| | EPSPS gene 1P101 | cagcagcagttacagtagct | 28 |
| Potato | PPX R144 | tgcgcctcgctttgtcttgt | 29 |
| | PPX A220 | attttacaggtgtttacgcc | 30 |

A limitation of the design constraints is that it is often hard to find a NGG sequence within 12 bp of the nucleotide being altered by ODM. This is significant because if this was the case, successful ODM would mean that subsequent cutting would not be possible because the protospacer seed sequence would be altered. Jinek et al. (2012) showed this was detrimental to cutting efficiency.

REFERENCES

LeCong et al 2013 Science: vol. 339 no. 6121 pp. 819-823.
Jinek et al 2012 Science. 337:816-21
Wang et al 2008 RNA 14: 903-913
Zhang et al 2013. Plant Physiol. 161: 20-27

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for introducing a gene repair oligonucleobase (GRON)-mediated mutation into a target deoxyribonucleic acid (DNA) sequence in a plant cell, comprising:
   delivery of a composition which induces single or double strand breaks and a GRON into the cell, wherein the GRON comprises one or more modifications selected from the group consisting of
   a reverse base at the 3' end thereof,
   one or more 2'O-methyl nucleotides at the 3' end thereof,
   one or more 2'O-methyl RNA nucleotides at the 5' end thereof,
   a 5' terminus cap, and
   one or more fluorescent dyes covalently attached thereto at the 5' or 3' end thereof;
   wherein the GRON is configured to mediate introduction of a targeted genetic change within the gene, and wherein delivery of the composition which induces single or double strand breaks and the GRON into the cell produces the targeted genetic change in the genome of the cell without incorporation of the GRON into the genome such that the cell is non-transgenic with respect to the targeted genetic change.

2. The method of claim 1, wherein the method further comprises synthesizing all or a portion of the GRON using nucleotide multimers.

3. The method of claim 1, wherein the target deoxyribonucleic acid (DNA) sequence is within the plant cell genome.

4. The method of claim 1, wherein the plant cell is obtained from a plant selected from the group consisting of canola, sunflower, corn, tobacco, sugar beet, cotton, maize, wheat, barley, rice, alfafa, barley, sorghum, tomato, mango, peach, apple, pear, strawberry, banana, melon, potato, carrot, lettuce, onion, soy bean, soya spp, sugar cane, pea, chickpea, field pea, faba bean, lentils, turnip, rutabaga, brussel sprouts, lupin, cauliflower, kale, field beans, poplar, pine, *eucalyptus*, grape, citrus, triticale, alfalfa, rye, oats, turf and forage grasses, flax, oilseed rape, mustard, cucumber, morning glory, balsam, pepper, eggplant, marigold, lotus, cabbage, daisy, carnation, tulip, iris, and lily.

5. The method of claim 1, wherein the target DNA sequence is an endogenous gene of the plant cell.

6. The method of claim 1, further comprising regenerating a plant having a mutation introduced by the GRON from the plant cell.

7. The method of claim 6, further comprising collecting seeds from the plant.

8. The method of claim 1, wherein the GRON is at least 100 bases in length.

9. The method of claim 1, wherein the GRON is at least 200 bases in length.

10. The method of claim 1, wherein the composition which induces single or double strand breaks is selected from the group consisting of a bleomycin-type antibiotic, a zinc finger nuclease, a Transcription Activator-Like Effector Nuclease (TALEN), a meganuclease, and a Clustered Regularly Interspaced Short Palindromic Repeat (CRISPR) nuclease.

11. The method of claim 8, wherein the composition which induces single or double strand breaks is selected from the group consisting of a bleomycin-type antibiotic, a zinc finger nuclease, a Transcription Activator-Like Effector Nuclease (TALEN), a meganuclease, and a Clustered Regularly Interspaced Short Palindromic Repeat (CRISPR) nuclease.

12. The method of claim 9, wherein the composition which induces single or double strand breaks is selected from the group consisting of a bleomycin-type antibiotic, a zinc finger nuclease, a Transcription Activator-Like Effector Nuclease (TALEN), a meganuclease, and a Clustered Regularly Interspaced Short Palindromic Repeat (CRISPR) nuclease.

* * * * *

SEQUENCE LISTING

```
<160> NUMBER OF SEQ ID NOS: 38

<210> SEQ ID NO 1
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphothioate linkage between nucleotides
<220> FEATURE:
<221> NAME/KEY: misc_feature
<222> LOCATION: (96)..(99)
<223> OTHER INFORMATION: Phosphothioate linkage between nucleotides

<400> SEQUENCE: 1
gtcgtgctgc ttcatgtggt cggggtagcg gctgaagcac tgcacgccgt aggtgaaggt      60
ggtcacgagg gtgggccagg gcacgggcag cttgccggtg g                         101

<210> SEQ ID NO 2
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
```

```
<222> LOCATION: (1)..(4)
<223> OTHER INFORMATION: Phosphothioate linkage between nucleotides
<220> FEATURE:
<221> NAME/KEY: misc_feature
<222> LOCATION: (98)..(101)
<223> OTHER INFORMATION: Phosphothioate linkage between nucleotides

<400> SEQUENCE: 2
gtcgtgctgc ttcatgtggt cggggtagcg gctgaagcac tgcacgccgt gggtgaaggt      60
ggtcacgagg gtgggccagg gcacgggcag cttgccggtg g                         101

<210> SEQ ID NO 3
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(4)
<223> OTHER INFORMATION: Phosphothioate linkage between nucleotides
<220> FEATURE:
<221> NAME/KEY: misc_feature
<222> LOCATION: (98)..(101)
<223> OTHER INFORMATION: Phosphothioate linkage between nucleotides

<400> SEQUENCE: 3
ccaccggcaa gctgcccgtg ccctggccca ccctcgtgac caccttcacc tacggcgtgc      60
agtgcttcag ccgctacccc gaccacatga agcagcacga c                         101

<210> SEQ ID NO 4
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(4)
<223> OTHER INFORMATION: Phosphothioate linkage between nucleotides
<220> FEATURE:
<221> NAME/KEY: misc_feature
<222> LOCATION: (98)..(101)
<223> OTHER INFORMATION: Phosphothioate linkage between nucleotides

<400> SEQUENCE: 4
ccaccggcaa gctgcccgtg ccctggccca ccctcgtgac caccttcacc cacggcgtgc      60
agtgcttcag ccgctacccc gaccacatga agcagcacga c                         101

<210> SEQ ID NO 5
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(4)
<223> OTHER INFORMATION: Phosphothioate linkage between nucleotides
<220> FEATURE:
<221> NAME/KEY: misc_feature
<222> LOCATION: (198)..(201)
<223> OTHER INFORMATION: Phosphothioate linkage between nucleotides

<400> SEQUENCE: 5
aagatggtgc gctcctggac gtagccttcg ggcatggcgg acttgaagaa gtcgtgctgc      60
```

```
ttcatgtggt cggggtagcg gctgaagcac tgcacgccgt aggtgaaggt ggtcacgagg    120
gtgggccagg gcacgggcag cttgccggtg gtgcagatga acttcagggt cagcttgccg    180
taggtggcat cgccctcgcc c                                              201
```

```
<210> SEQ ID NO 6
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(4)
<223> OTHER INFORMATION: Phosphothioate linkage between nucleotides
<220> FEATURE:
<221> NAME/KEY: misc_feature
<222> LOCATION: (198)..(201)
<223> OTHER INFORMATION: Phosphothioate linkage between nucleotides

<400> SEQUENCE: 6
```

```
aagatggtgc gctcctggac gtagccttcg ggcatggcgg acttgaagaa gtcgtgctgc    60
ttcatgtggt cggggtagcg gctgaagcac tgcacgccgt gggtgaaggt ggtcacgagg   120
gtgggccagg gcacgggcag cttgccggtg gtgcagatga acttcagggt cagcttgccg   180
taggtggcat cgccctcgcc c                                             201
```

```
<210> SEQ ID NO 7
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(4)
<223> OTHER INFORMATION: Phosphothioate linkage between nucleotides
<220> FEATURE:
<221> NAME/KEY: misc_feature
<222> LOCATION: (198)..(201)
<223> OTHER INFORMATION: Phosphothioate linkage between nucleotides

<400> SEQUENCE: 7
```

```
gggcgagggc gatgccacct acggcaagct gaccctgaag ttcatctgca ccaccggcaa    60
gctgcccgtg ccctggccca ccctcgtgac caccttcacc tacggcgtgc agtgcttcag   120
ccgctacccc gaccacatga agcagcacga cttcttcaag tccgccatgc ccgaaggcta   180
cgtccaggag cgcaccatct t                                             201
```

```
<210> SEQ ID NO 8
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(4)
<223> OTHER INFORMATION: Phosphothioate linkage between nucleotides
<220> FEATURE:
<221> NAME/KEY: misc_feature
<222> LOCATION: (198)..(201)
<223> OTHER INFORMATION: Phosphothioate linkage between nucleotides

<400> SEQUENCE: 8
```

```
gggcgagggc gatgccacct acggcaagct gaccctgaag ttcatctgca ccaccggcaa    60
gctgcccgtg ccctggccca ccctcgtgac caccttcacc cacggcgtgc agtgcttcag   120
ccgctacccc gaccacatga agcagcacga cttcttcaag tccgccatgc ccgaaggcta   180
cgtccaggag cgcaccatct t                                             201
```

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Lys Lys Arg Lys Val
1               5

<210> SEQ ID NO 10
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: misc_feature
<222> LOCATION: (1)..(20)
<223> OTHER INFORMATION: n is a, c, g, or t

<400> SEQUENCE: 10

```
nnnnnnnnnn nnnnnnnnnn gttttagagc tagaaatagc aagttaaaat aaggctagtc    60
cgttatgttc ttgaaaaaag tgagtggcac cgagtcggtg gtgcttttt              110
```

<210> SEQ ID NO 11
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(32)
<223> OTHER INFORMATION: a, c, u, g, unknown or other
<220> FEATURE:
<221> NAME/KEY: misc_feature
<222> LOCATION: (3)..(32)
<223> OTHER INFORMATION: n is a, c, g, or u

<400> SEQUENCE: 11

```
acnnnnnnnn nnnnnnnnnn nnnnnnnnnn nnguuuaga gcuaugcu                 48
```

<210> SEQ ID NO 12
<211> LENGTH: 67
<212> TYPE: DNA
<213> ORGANISM: Artificial Sequence
<220> FEATURE:
<223> OTHER INFORMATION: Description of Combined DNA/RNA Molecule:
      Synthetic oligonucleotide

<400> SEQUENCE: 12

```
agcauagcaa guuaaaauaa ggcuaguccg uuaucaacuu gaaaaagugg caccgagucg    60
``` gugcuuu 67

<210> SEQ ID NO 13
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: n is a, c, g, or u

<400> SEQUENCE: 13
nnnnnnnnnn nnnnnnnnnn guuuuagagc uagaaauagc aaguuaaaau aaggcuaguc   60
cg                                                                 62

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcgtgaccac cttcacccac ggc                                          23

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Val Thr Thr Phe Thr Tyr
1               5

<210> SEQ ID NO 16
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtggaaagga cgaaacaccg ggtcttcgag aagacctgtt ttagagctag aaatagcaag   60
ttaaaataag gctagtccgt tttt                                         84

<210> SEQ ID NO 17
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
aaaaacggac tagccttatt ttaacttgct atttctagct ctaaaacagg tcttctcgaa    60
gacccggtgt tcgtcctttt ccac                                           84
```

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(24)
<223> OTHER INFORMATION: a, c, t, g, unknown or other
<220> FEATURE:
<221> NAME/KEY: misc_feature
<222> LOCATION: (6)..(24)
<223> OTHER INFORMATION: n is a, c, g, or t

<400> SEQUENCE: 18

```
caccgnnnnn nnnnnnnnnn nnnn                                           24
```

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(23)
<223> OTHER INFORMATION: a, c, t, g, unknown or other
<220> FEATURE:
<221> NAME/KEY: misc_feature
<222> LOCATION: (5)..(23)
<223> OTHER INFORMATION: n is a, c, g, or t

<400> SEQUENCE: 19

```
aaacnnnnnn nnnnnnnnnn nnnc                                           24
```

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Thr Ala Met Arg Pro Leu Thr Val Ala Ala Val
1               5                   10
```

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
actgcaatgc ggccattgac agcagctgtt actgctgctg g                        41
```

<210> SEQ ID NO 22
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 22
ccgctgccgt tactgctgca                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cggctgcagt tactgctgct                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ccgctgcagt tactgctgca                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccgctgcagt tacagctgca                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagctgctgt aacagccgct                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cagcagcagt tgctgtagct                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 28
cagcagcagt tacagtagct                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgcgcctcgc tttgtcttgt                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
attttacagg tgtttacgcc                                                    20

<210> SEQ ID NO 31
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-Me modified nucleotide
<220> FEATURE:
<221> NAME/KEY: modified_base
<222> LOCATION: (11)..(71)
<223> OTHER INFORMATION: 2'-O-Me modified nucleotide

<400> SEQUENCE: 31
uucauguggu cggggtagcg gctgaagcac tgcacgccgt aggtgaaggt ggtcacgagg         60
gtgggccagg g                                                             71

<210> SEQ ID NO 32
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-Me modified nucleotide
<220> FEATURE:
<221> NAME/KEY: modified_base
<222> LOCATION: (11)..(71)
<223> OTHER INFORMATION: 2'-O-Me modified nucleotide

<400> SEQUENCE: 32
uucauguggu cggggtagcg gctgaagcac tgcacgccgt gggtgaaggt ggtcacgagg         60
gtgggccagg g                                                             71

```
<210> SEQ ID NO 33
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-Me modified nucleotide
<220> FEATURE:
<221> NAME/KEY: modified_base
<222> LOCATION: (11)..(71)
<223> OTHER INFORMATION: 2'-O-Me modified nucleotide

<400> SEQUENCE: 33
gcugcccgug ccctggccca ccctcgtgac caccttcacc tacggcgtgc agtgcttcag    60
ccgctacccc g                                                         71

<210> SEQ ID NO 34
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-Me modified nucleotide
<220> FEATURE:
<221> NAME/KEY: modified_base
<222> LOCATION: (11)..(71)
<223> OTHER INFORMATION: 2'-O-Me modified nucleotide

<400> SEQUENCE: 34
gcugcccgug ccctggccca ccctcgtgac caccttcacc cacggcgtgc agtgcttcag    60
ccgctacccc g                                                         71

<210> SEQ ID NO 35
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(9)
<223> OTHER INFORMATION: 2'-O-Me modified nucleotide
<220> FEATURE:
<221> NAME/KEY: modified_base
<222> LOCATION: (11)..(71)
<223> OTHER INFORMATION: 2'-O-Me modified nucleotide

<400> SEQUENCE: 35
uucauguggu cggggtagcg gctgaagcac tgcacgccgt aggtgaaggt ggtcacgagg    60
gtgggccagg g                                                         71

<210> SEQ ID NO 36
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(9)
```

```
<223> OTHER INFORMATION: 2'-O-Me modified nucleotide
<220> FEATURE:
<221> NAME/KEY: modified_base
<222> LOCATION: (11)..(71)
<223> OTHER INFORMATION: 2'-O-Me modified nucleotide

<400> SEQUENCE: 36
uucauguggu cggggtagcg gctgaagcac tgcacgccgt gggtgaaggt ggtcacgagg    60
gtgggccagg g                                                        71

<210> SEQ ID NO 37
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(9)
<223> OTHER INFORMATION: 2'-O-Me modified nucleotide
<220> FEATURE:
<221> NAME/KEY: modified_base
<222> LOCATION: (11)..(71)
<223> OTHER INFORMATION: 2'-O-Me modified nucleotide

<400> SEQUENCE: 37
gcugcccgug ccctggccca ccctcgtgac caccttcacc tacggcgtgc agtgcttcag    60
ccgctacccc g                                                        71

<210> SEQ ID NO 38
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(9)
<223> OTHER INFORMATION: 2'-O-Me modified nucleotide
<220> FEATURE:
<221> NAME/KEY: modified_base
<222> LOCATION: (11)..(71)
<223> OTHER INFORMATION: 2'-O-Me modified nucleotide

<400> SEQUENCE: 38
gcugcccgug ccctggccca ccctcgtgac caccttcacc cacggcgtgc agtgcttcag    60
ccgctacccc g                                                        71
```